(12) United States Patent
Ogle et al.

(10) Patent No.: US 8,048,042 B2
(45) Date of Patent: Nov. 1, 2011

(54) MEDICAL ARTICLES INCORPORATING SURFACE CAPILLARY FIBER

(75) Inventors: Matthew F. Ogle, Oronoco, MN (US); Thomas F. Hinnenkamp, White Bear Lake, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1339 days.

(21) Appl. No.: 10/781,503

(22) Filed: Feb. 18, 2004

(65) Prior Publication Data
US 2005/0021152 A1 Jan. 27, 2005

Related U.S. Application Data

(60) Provisional application No. 60/489,288, filed on Jul. 22, 2003.

(51) Int. Cl.
*A61M 25/00* (2006.01)
(52) U.S. Cl. ......... 604/264; 604/265; 604/269; 604/523
(58) Field of Classification Search .................. 604/264, 604/265, 266, 269, 523
See application file for complete search history.

(56) References Cited

U.S. PATENT DOCUMENTS

| | | | |
|---|---|---|---|
| 2,972,350 A * | 2/1961 | Marta Deker | ............... 604/362 |
| 4,044,404 A | 8/1977 | Martin et al. | |
| 4,512,338 A | 4/1985 | Balko et al. | |
| 4,550,126 A | 10/1985 | Lorenz | |
| 4,793,348 A | 12/1988 | Palmaz | |
| 4,817,600 A | 4/1989 | Herms et al. | |
| 4,832,055 A | 5/1989 | Palestrant | |
| 5,059,205 A | 10/1991 | El-Nounou et al. | |
| 5,156,601 A * | 10/1992 | Lorenz et al. | ............... 604/307 |
| 5,200,248 A | 4/1993 | Thompson et al. | |
| 5,350,398 A | 9/1994 | Pavenik et al. | |
| 5,370,657 A | 12/1994 | Irie | |
| 5,407,673 A | 4/1995 | Reich et al. | |
| 5,540,707 A | 7/1996 | Ressemann et al. | |
| 5,569,463 A | 10/1996 | Helmus et al. | |
| 5,651,765 A | 7/1997 | Haworth et al. | |
| 5,704,910 A | 1/1998 | Humes | |
| 5,722,947 A | 3/1998 | Jeppsson et al. | |
| 5,782,791 A | 7/1998 | Peterson et al. | |
| 5,807,306 A | 9/1998 | Shapland et al. | |
| 5,836,868 A | 11/1998 | Ressemann et al. | |
| 5,911,704 A | 6/1999 | Humes | |
| 5,914,125 A | 6/1999 | Andrews et al. | |
| 5,919,145 A | 7/1999 | Sahatjian | |
| 5,938,645 A | 8/1999 | Gordon | |
| 5,941,869 A | 8/1999 | Patterson et al. | |

(Continued)

OTHER PUBLICATIONS

Fasseas et al., "Distal protection devices during percutaneous coronary and carotid interventions," current Controlled Trials in Cardiovascular Medicine, vol. 2, No. 6, Dec. 2002, 5 pages.

(Continued)

*Primary Examiner* — Bhisma Mehta

(57) ABSTRACT

Medical devices are described that comprise surface capillary (SCF) fibers, which can impart desirable properties to the devices. For example, implantable prostheses are described comprising SCF fibers. In other embodiments, catheters are described having SCF fibers along the surface of the catheters. In addition, SCF fibers can be useful for the delivery of bioactive agents in association with the fibers. Due to the fluid flow capabilities of the fibers, medical devices are described that incorporate fiber matrices to facilitate blood delivery to cells within the structure.

25 Claims, 5 Drawing Sheets

U.S. PATENT DOCUMENTS

| | | | |
|---|---|---|---|
| 5,972,019 | A | 10/1999 | Engelson et al. |
| 5,972,505 | A | 10/1999 | Phillips et al. |
| 5,977,429 | A | 11/1999 | Phillips et al. |
| 6,066,149 | A * | 5/2000 | Samson et al. ................. 606/159 |
| 6,099,864 | A | 8/2000 | Morrison et al. |
| 6,103,376 | A | 8/2000 | Phillips et al. |
| 6,123,681 | A | 9/2000 | Brown, III |
| 6,160,084 | A | 12/2000 | Langer et al. |
| 6,231,589 | B1 | 5/2001 | Wessman et al. |
| 6,245,088 | B1 | 6/2001 | Lowery |
| 6,245,089 | B1 | 6/2001 | Daniel et al. |
| 6,254,563 | B1 | 7/2001 | Macoviak et al. |
| 6,263,880 | B1 | 7/2001 | Parker et al. |
| 6,267,776 | B1 | 7/2001 | O'Connell |
| 6,273,901 | B1 | 8/2001 | Whitcher et al. |
| 6,306,163 | B1 | 10/2001 | Fritz |
| 6,346,116 | B1 | 2/2002 | Brooks et al. |
| 6,350,253 | B1 * | 2/2002 | Deniega et al. ........... 604/164.02 |
| 6,364,895 | B1 | 4/2002 | Greenhalgh |
| 6,364,896 | B1 | 4/2002 | Addis |
| 6,368,338 | B1 | 4/2002 | Konya et al. |
| 6,368,344 | B1 | 4/2002 | Fitz |
| 6,371,969 | B1 | 4/2002 | Tsugita et al. |
| 6,371,970 | B1 | 4/2002 | Khosravi et al. |
| 6,391,044 | B1 | 5/2002 | Yadav et al. |
| 6,391,300 | B1 | 5/2002 | Rose et al. |
| 6,395,029 | B1 | 5/2002 | Levy |
| 6,420,622 | B1 | 7/2002 | Johnston et al. |
| 6,450,989 | B2 | 9/2002 | Dubrul et al. |
| 6,458,119 | B1 | 10/2002 | Berenstein et al. |
| 6,485,501 | B1 | 11/2002 | Green |
| 6,491,965 | B1 | 12/2002 | Berry et al. |
| 6,527,746 | B1 | 3/2003 | Oslund et al. |
| 6,602,271 | B2 | 8/2003 | Adams et al. |
| 6,605,111 | B2 | 8/2003 | Bose et al. |
| 6,645,223 | B2 | 11/2003 | Boyl et al. |
| 6,652,505 | B1 | 11/2003 | Tsugita et al. |
| 6,676,682 | B1 | 1/2004 | Tsugita et al. |
| 6,878,153 | B2 | 4/2005 | Linder et al. |
| 6,929,626 | B2 * | 8/2005 | DiCarlo et al. ................ 604/249 |
| 7,326,196 | B2 * | 2/2008 | Olsen et al. .................... 604/523 |
| 2002/0072550 | A1 | 6/2002 | Brady et al. |
| 2003/0018306 | A1 * | 1/2003 | Bucay-Couto et al. ....... 604/265 |
| 2003/0040692 | A1 * | 2/2003 | Rothwell et al. ................ 602/48 |
| 2004/0093015 | A1 | 5/2004 | Ogle |

OTHER PUBLICATIONS

"Smart suture is first application of novel MIT polymer," from website http://web/mit.edu/newsoffice/nr/2002/langer-suture.html, Apr. 25, 2002, 3 pages.

Reichenspurner et al., "Particulate emboli capture by an intra-aortic filter device during cardia surgery," The Journal of Thoracic & Cardiovascular Surgery, vol. 119(2), Feb. 2000, pp. 233-241.

Harringer et al., "Capture of particulate emboli during cardiac procedures in which aortic cross-clamp is used," The Society of Thoracic Surgeons, vol. 70, 2000, pp. 1119-1123.

4DG? Fibers: http://web.archive.org/web/201103007001/http://fitfibers.com/4DG_Fibers.htm; (Oct. 30, 2001).

Fiber Innovative Technology: biocomponent and specialty fibers; FIT Capabilities; hrrp://web.archive.orglweb/200102170408481/http://www.fitfibers.com/capabilities.htm (Feb. 17, 2001).

Fiber Innovation Technology: biocomponent and specialty fibers; FIT Products; http://web.archive.org/web/20010408003529/http://www.fitfibers.com/product.htm, (Apr. 8, 2001).

Vaughn et al., "Expanded Surface Area Fibers: A Means for Medical Product Enhancement," Journal of Industrial Textiles, 2001; 30(4):303-310.

* cited by examiner

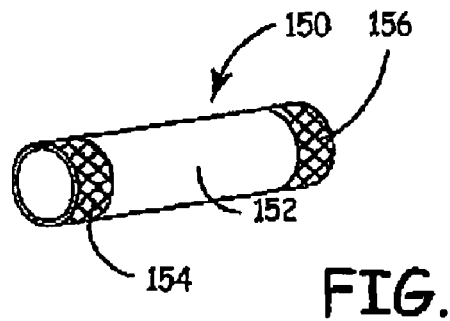
FIG. 3
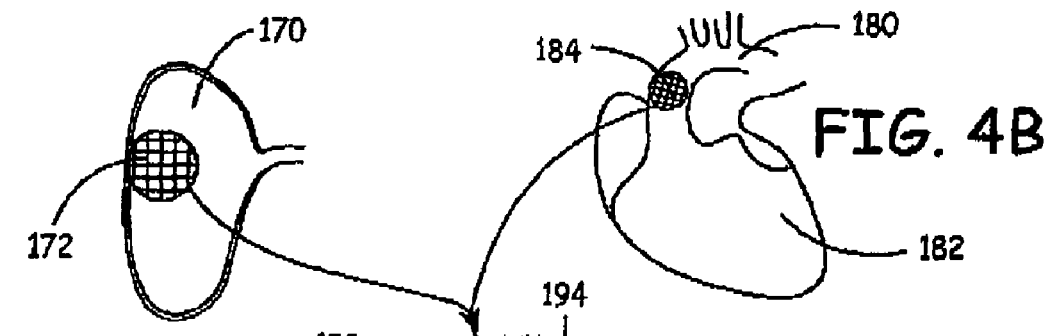
FIG. 4A
FIG. 4B
FIG. 4C
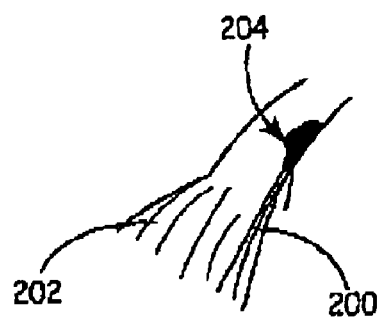
FIG. 5

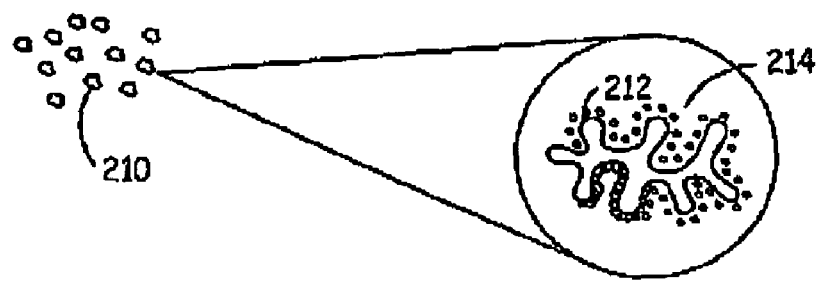
FIG. 6
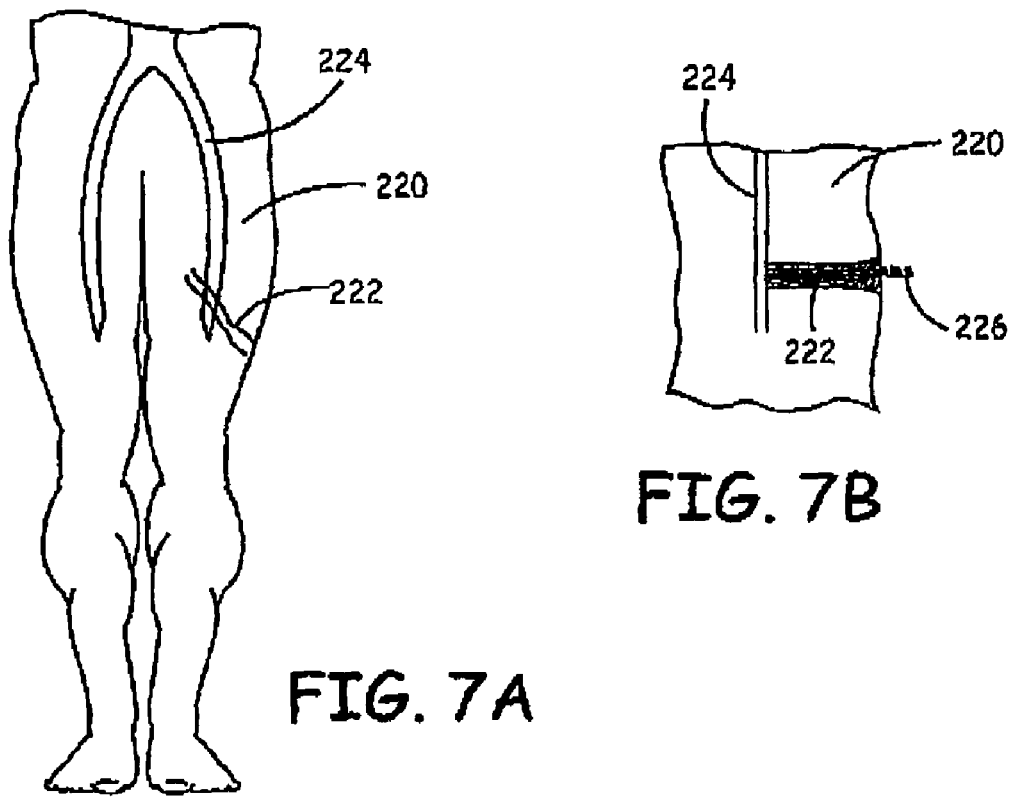
FIG. 7B
FIG. 7A

MEDICAL ARTICLES INCORPORATING SURFACE CAPILLARY FIBER

CROSS REFERENCE TO RELATED APPLICATIONS

This application claims priority to U.S. provisional patent application Ser. No. 60/489,288 to Ogle et al. filed on Jul. 22, 2003, entitled "Microchanneled Medical Article," incorporated herein by reference.

FIELD OF THE INVENTION

The invention relates to medical devices suitable for contacting a patient's bodily fluids. In particular, the invention relates to medical devices, such as prostheses, catheters, synthetic organs, biocompatible substrates, drug delivery elements, vascular closure devices or aneurysm repair matrices, that incorporate surface capillary fibers in or on the medical device or a portion thereof. Also, the invention relates to medical devices with surface capillary fibers that have a bioactive agent associated with them as well as methods for delivery of bioactive agents. Furthermore, the invention relates to approaches for applying these fibers to medical devices suitable for a variety of clinical applications.

BACKGROUND OF THE INVENTION

A variety of medical devices/medical articles are designed particularly for contact with a patient's bodily fluids. The duration of this contact may be relatively short, as is typical with devices used in endovascular procedures, or may be long term, which is typical with artificial organs implanted into the body of a recipient and with other implanted prostheses. Some devices, such as catheters, other percutaneous devices or components thereof, can have either short term or relatively long-term contact.

Prostheses, i.e., prosthetic articles, are used to repair or replace damaged or diseased organs, tissues and other structures in humans and animals. Prostheses generally are biocompatible since they are typically implanted for extended periods of time. Examples of prostheses include, without limitation, prosthetic hearts, prosthetic heart valves, ligament repair materials, vessel repair and replacement materials, stents, and surgical patches. Development of artificial organs has been spurred by the sever shortage of donor organs. To date, artificial heart (implants), artificial liver (extracorporeal) and artificial kidney (extracorporeal) have been used in the clinic.

Contact of articles with bodily fluids creates a number of functional and biocompatibility challenges. Some challenges associated with these medical devices are as follows; blood compatibility, infection control, rejection, and nutrient transfer (i.e. passing oxygenated blood to devices, or transport of fluid on blood for bio-active benefit). All these challenges can reduce the relative degree of success of the medical articles and corresponding medical procedures, for example, to repair, treat or replace an injured or diseased native structure.

When blood compatibility is not achieved, an interaction between a medical device and the patient's bodily fluids can result in a complex cascade of events creating a biological reaction, such as aggregated thrombus formation or "clot." Thrombus formation can be the first event a medical device experiences when placed into contact with the blood. This biological reaction can be in response to a toxic substance or to an irregular surface structure, which causes red blood cells to lyse thereby inducing a nexus for blood clotting and non-specific fibrin aggregation on the material. This primary event can precipitate secondary diseases states such as embolization, fibrolitic overgrowth, restenosis, and calcification. The secondary diseases can be a relatively early event occurring within minutes to hours after implantation. While very important, blood compatibility is not the only biological complication that can result from use of a medical article. For example, devices that are very blood compatible may still be faced with problems relating to infection.

Introduction of medical articles or devices into contact with bodily fluids creates an increased a risk of bacterial colonization. These infections can affect the function of the medical article and may cause increased morbidity and mortality, which may or may not be related to the function of the medical device. For example, infection can affect the adhesive properties of a glue, which can result in failure of a medical device. Beyond mechanical and functional considerations, often contaminated devices and the surrounding tissue are removed to prevent pailure of the device and/or spread of the infection. In the worst cases, sepses sets in and the entire system is compromised. If the patient contracts sepses, the patient can die of secondary organ failure. These concerns are further propagated by the existence of antibiotic resistant strains of bacteria.

The body uses the biological mechanisms brought to bear by the immune system to deal with infections. Unfortunately, the immune system cannot necessarily distinguish harmful foreign invaders from helpful medical articles. The attack of medical devices or prosthetic organs by the immune system is termed "rejection".

In the immune system, each protector cell (e.g., B cells, Macrophages, and T cells) in the body is genetically programmed to recognize a specific molecular marker on an invading material or organism (antigens). When one of these cells encounters a mismatched antigen, the cell attempts to engulf the foreign material and expresses the antigen motifs on its cell surface. When the response is complete, suppressor T cells help shut down the immune response, but when the material is not resorbable or too large, a chronic immune reaction or rejection of the material can ensue. Rejection can necessitate treatment with expensive drugs that also may have undesirable side effects. In extreme cases, rejection can necessitate removal of the medical device.

Another challenge of device implantation can be lack of nutrient transport. This is a particular challenge for tissue engineering and organogenesis where complex three dimensional structures are fabricated that may require not only structural integrity and functioning architecture but also require delivery of biologically essential fluids, e.g., oxygenated blood to the cells integral to the structure. Efforts to promote vascularization or other types of fluid transport systems for medical devices has seen limited success.

These challenges are at the corner stone of device and materials interaction, and the appropriate handling of these challenges can be helpful in making better, longer lasting, more successful devices to provide treatment or to replace diseased or injured body parts.

SUMMARY OF THE INVENTION

In a first aspect, the invention relates to a prosthetic medical device comprising an SCF fiber bound within an implantable structure.

In a further aspect, the invention relates to medical device comprising an SCF fiber and a quantity of bioactive agent associated with the SCF fiber.

In another aspect, the invention relates to a tubular medical device comprising a tubular substrate having an interior surface and an exterior surface. In these embodiments, at least one SCF fiber is associated with at least a portion of one of the surfaces.

Furthermore, the invention relates to a medical device comprising a non-porous surface at least a portion of which is covered with SCF fibers.

In addition, the invention relates to an artificial organ comprising SCF fibers and viable cell within a monolithic structure.

In further aspects, the invention relates to an aneurysm repair matrix comprising a mesh formed with an SCF fiber configured to envelope an aneurysm.

In an additional aspect, the invention relates to a method for delivering a bioactive agent. The method comprises contacting a patient's body fluids/tissues with an SCF fiber associated with the bioactive agent.

BRIEF DESCRIPTION OF THE DRAWINGS

FIG. 3 is a perspective view of a vascular prosthesis comprising SCF fibers at attachment regions.

FIG. 4A is a schematic view of a lung with a surgical patch comprising SCF fibers.

FIG. 4B is a schematic view of an aorta with a surgical patch comprising SCF fibers.

FIG. 4C is a schematic expanded view of an SCF fiber adhered with an adhesive to a tissue.

FIG. 5 is a view of a tendon with a patch comprising SCF fibers.

FIG. 6 is a schematic view of SCF particle with a bioactive agent with an insert showing a cartoon of a fiber with the bioactive agent.

FIG. 7A is a view of a patient's leg with a puncture wound made to access a vein with a catheter.

FIG. 7B is an expanded view of the puncture wound plugged with a vascular closure device comprising SCF fibers.

DETAILED DESCRIPTION OF THE INVENTION

Figure 1A:
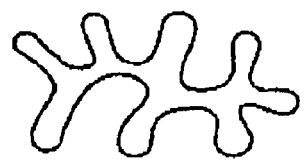
FIG. 1A is a schematic cross section of an SCF fiber.

Improved medical devices have surface capillary fibers (SCF) to impart desired properties to the medical device. In particular, the increased surface area and fluid moving capability of the SCF fibers can provide desirable features to a medical device incorporating these materials. The advantages of these fibers can be combined with other features that are contributed by additional materials that are incorporated into the medical device along with the SCF fibers. In particular, prostheses, i.e., implantable medical devices, can have SCF fibers to contribute particular features to the device generally relating to the high surface area of the fibers. Furthermore, percutaneous devices, such as catheters and the like, can advantageously incorporate SCF fibers. In some embodiments, SCF fibers associated with medical devices can be used to deliver bioactive agents. Due to the high surface area of the fibers, SCF fibers can hold in a controlled way larger quantities of bioactive agents compared with other types of fibers. In some embodiments, the large surface areas of the fibers can be used for the controlled transport and/or delivery of fluid, such as blood, at desired locations within or adjacent a medical device. The advantages of SCF fibers can offer improved clinical outcomes in the areas of filtration, homeostasis, drug delivery, adhesion through mechanical interlocking, and other areas.

A number of medical articles can be used to contact bodily fluids of a patient. Relevant medical articles generally incorporate one or more biocompatible materials that are intended to contact the patient's biological fluids and/or tissues. Bodily fluids include, for example, blood, plasma, serum, interstitial fluids, central nervous system fluid, saliva and urine. Patients of interest, in particular, include, for example, human patients as well as livestock, pets and other valuable animals. Biocompatible materials generally are non-toxic, non-carcinogenic and blood compatible and do not induce hemolysis or a significant immunological response.

Desired medical devices can comprise SCF fibers as the only structural component. For example, the device can comprise a single fiber or a plurality of fibers, which can be multiple entwined fibers, woven fibers, bundled fibers, separately attached fibers or the like. However, in many embodiments of interest, the SCF fibers are combined with one or more other material to form the medical device. These other materials can be, for example, tissue, polymers, ceramics and/or metals.

SCF fibers are characterized by surface channels or capillaries formed within the surface of the fiber. Surface capillaries are characterized by having a portion of the capillary exposed at the surface of the fiber along the length of the fiber. The surface capillaries result in significant increase in the surface area of the fibers relative to fibers with a smooth surface and the same diameter. The surface capillaries generally run along the length of the fiber. In some embodiments, the surface of the fiber has a plurality of surface channels or capillaries along the length of the fiber. An SCF fiber can have surface channels that essentially make up a large fraction of the bulk of the fiber such that little if any of the interior mass of the fiber is not associated with walls of one or more surface capillaries.

In particular, the SCF fiber substrate can be formed with a relatively complex cross-sectional geometry. In some embodiments, the geometry of the fibers used in particular medical devices have surface capillaries that can move relatively large amounts of fluid at significant rates. Suitable fibers include commercially available 4DG™ fibers (Fiber Innovation Technology, Inc., Johnson City, Tenn.) but would also include new advanced geometries to provide for greater fluid transport or absorption or wetting capabilities. In particular, geometries can be selected to be particularly advantageous for the particular application. Suitable approaches for the manufacture of the SCF are described in, for example, U.S. Pat. No. 5,200,248 to Thompson et al., entitled "Open Capillary Structures, Improved Process For Making Channel Structures And Extrusion Die For Use Therein," incorporated herein by reference. Alternative fiber structures are described below.

Furthermore, the selection of the polymer composition for the fiber can provide further flexibility to the properties of the fiber for a particular application. For example the fiber polymer composition can modulate the hydrophobic or hydrophilic nature of the device, or the polymer may dissolve controlled released drugs. Furthermore, the fibers can incorporate coatings or the like that can further modify the fiber properties. Thus, the incorporation of SCF into medical devices offers desirable strategies to develop improved implantable components. The polymer composition for the SCF fibers generally can incorporate certain desired properties of medical polymers, such as established biostability, bioerosion, strength, flexibility, and compressibility.

In some embodiments, the SCF fibers are 4DG™ fibers, with sizes ranging from about 1.5 denier to about 1000 denier in size. The size of the fibers can influence the mechanical, structural, filtration, compressablilty and fluid dynamic properties of the device. Thus, the selected fiber size may be different for different applications.

Medical devices incorporating SCF fibers can be effective for the delivery of bioactive agents in the vicinity of the medical device. By incorporating the bioactive agents within the surface capillaries of the fibers, the volume of the volume of the bioactive agent can be significantly greater than can be readily associated with a conventional fiber surface of the same length. The form of the bioactive agent can be selected to yield the desired release profile. For gradual release of the bioactive agent, the agent can be combined with a controlled release agent. In other embodiments, the formation of the bioactive agent can be selected to yield an appropriate release rate over shorter periods of time. The particular contouring of the fiber can similarly influence the release rate due to surface effects.

Suitable bioactive agents can be thrombolytic agents such as tissue plasminogen activator (tPA) or urokinase, or the agents can release mild acid (possibly along with a neutralizing base, such as bicarbonate) or anti-calcification enzymes such as osteopontin to resorb calcific plaque. In other embodiments, the device can release $O_2$ and/or sugars to nourish the patient's brain cells. In further embodiments, the device can release vasodilators such as NO or heparin to increase the available $O_2$ transport. In additional embodiments, the device can release growth factor, which could improve healing or create new vessels. In further embodiments, the device can release viral vectors, which transfected the surrounding cell to up regulate the release a polypeptide compound for extended therapy (e.g., tPA). Specifically, for protein/polypeptide based agents, the delivery of a gene (nucleic acid) encoding the agent in a vector, such as a viral vector, to promote in vivo expression of the protein is an alternative to the delivery of the protein itself. Delivery of vectors for desired polypeptides is described further below. The device similarly can be designed to release a plurality of these agents.

In general, the SCF can be incorporated into medical devices alone or in combination with other appropriate materials, such as polymers, ceramics, metals, tissues, biological macromolecules and other compositions. For example, the SCF can be woven into a material and/or secured together with an adhesive. In other embodiments, the SCF can be attached to a scaffold or the like that provides a structural framework. If other materials are included in the device, the SCF can be a relatively minor component supplied for drug delivery or to impart other desirable properties to the device or the SCF can be a major structural component that imparts significant structural properties to the device. The SCF can be combined with other materials, for example, through mechanical connection, such as interweaving, through adhesives and or chemical bonding, which can be covalent or non-covalent chemical bonding. The use of SCF fibers in the formation of embolism protection devices is described further in copending U.S. Provisional Patent Application Ser. No. 60/489,044 to Ogle et al., entitled "Embolism Protection System," incorporated herein by reference.

In general, the fibers can be associated with other materials with adhesives, mechanical binding, chemical bonding, blending or other appropriate approach. The approach used in assembling the components generally is selected to provide for the desired functionality of the components following the assembly process. Generally, conventional approach for medical device fabrication can be adapted to provide the SCF fibers in a desired configuration within the device or component thereof. The assembly process is performed under suitable antiseptic conditions for the components that contact bodily fluids in use. Alternatively or additionally, the device or components thereof can be sterilized following assembly using, for example, radiation, such as electron beam radiation, ultraviolet radiation or x-ray radiation, sterilizing liquids, such as alcohols, peroxides, aldehydes or any of a variety of other sterilizing liquids and/or sterilizing gases, such as ozone.

The SCF fibers can be advantageously incorporated into any of a variety of medical device that contact bodily fluids. Certain embodiments are of particular interest and are discussed further herein. For example, SCF fibers can in particular be incorporated within prostheses designed for implantation into a patient. The SCF fibers can provide one or more desirable attributes for these embodiments. In some embodiments, the SCF fibers are provided with a medical adhesive to facilitate anchoring of the prosthesis with the adhesive to provide a stronger adhesive bond. In other embodiments, the SCF fibers are provided in the prosthesis to yield improved fluid flow through the device or a portion thereof. In still further embodiments, the SCF fibers provide improved colonization by viable cells by the presence of a protected environment within the surface channels for cellular colonization. Viable cells can be associated with the device prior to implantation and/or the device can be colonized by native cells following implantation. In some catheter application, the incorporation of fibers on the interior surface of the catheter can moderate the fluid flow properties in desirable ways. In various applications, the SCF fibers can be advantageously used to deliver biologically active agents. Due to these and other advantages, SCF fibers can be used to form a range of improved medical devices.

Medical Devices

A medical device generally can be as an instrument, apparatus, implement, machine, contrivance, implant, in vitro reagent, or other similar or related article, including a component part, or accessory which is intended for use in the diagnosis of disease or other conditions, or in the cure, mitigation, treatment, or prevention of disease. Medical devices of particular interest are suitable for contacting bodily fluids in a suitable sterile environment and comprise at least a portion that is biocompatible and are referred to as biocompatible medical devices.

Relevant biocompatible medical devices include all medical devices that are designed for contacting bodily fluids. This contact with bodily fluids can be corporeal, i.e. within the patient's body or extracorporeal, i.e., in which the bodily fluid is circulated out from the body into a device for treatment or other processing, such as dialysis or filtering. These biocompatible articles can be made from the biocompatible materials described below. The corporeal biocompatible medical devices can be organized roughly into three groups: implanted devices, percutaneous devices and cutaneous devices. Implanted devices broadly include articles that are fully implanted in a patient, i.e., are completely internal, when in use. Percutaneous devices include items that penetrate the skin, thereby extending from outside the body into the body. Cutaneous devices are superficially applied for example, as a moist membrane within a patient's mouth or on a wound.

Implanted devices include, without limitation, prostheses such as pacemakers, electrical leads such as pacing leads, defibrillators, artificial organs, such as artificial hearts and artificial livers, ventricular assist devices, anatomical reconstruction prostheses such as breast implants, artificial heart valves, heart valve stents, pericardial patches, surgical patches, coronary stents, vascular grafts, vascular and structural stents, vascular reinforcements, vascular or cardiovascular shunts, biological conduits, pledgets, suture, annuloplasty rings, stents, staples, valved grafts, dermal grafts for wound healing, orthopedic spinal implants, orthopedic pins, intrauterine devices (IUDs), urinary stents, maxial facial reconstruction plating, dental implants, intraocular lenses, clips, sternal wires, bone, skin, ligaments, tendons, and combinations thereof.

Percutaneous devices include, without limitation, catheters of various types, cannulas, surgical instruments such as forceps, retractors, needles, and gloves, and catheter cuffs. Catheters can be used for accessing various bodily systems such as the vascular system, the gastrointestinal tract, or the urinary system. Extracorporeal devices that contact bodily fluids generally are used along with percutaneous device, and the SCF fibers can be used in connection with the percutaneous components and/or the fluid processing components of the overall device. Cutaneous devices include, without limitation, dental hardware, such as bridge supports and bracing components, wound patches and the like.

Devices used in cardiology procedures include, for example, distal protection devices to prevent ischemic event associated with embolus. Physicians also use a variety of medical devices to correct problems associated with the cardiovascular/vascular system, urinary tract, the neurological system, orthopedic elements, etc. While in principle SCF fibers can be used in any of the medical devices described above, a few medical devices are of particular interest. Such devices of particular interest include, for example, embolic protection devices, vascular closure devices, aneurysm repair device, catheters, artificial livers, artificial heart muscle, drug delivery devices, synthetic nerves, biological adhesive attachment structures, and orthopedic components, such as tendon repair devices. Suitable embodiments of embolism protection devices are described further in copending U.S. patent application Ser. No. 10/414,909 now U.S. Pat. No. 7,303,575 to Ogle, entitled "Embolism Protection Devices," incorporated herein by reference and copending provisional U.S. Patent Application Ser. No. 60/489,044, filed Jul. 22, 2003 to Ogle et al., entitled "Embolism Protection Device," incorporated herein by reference. Other specific medical devices of particular interest are described further below.

SCF Fibers

Figure 1B:
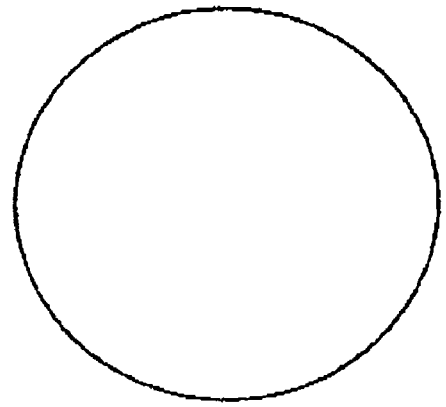
FIG. 1B is a schematic cross section of a fiber without surface capillaries that has an approximately the same surface area as the fiber of FIG. 1A.
Figure 2A:
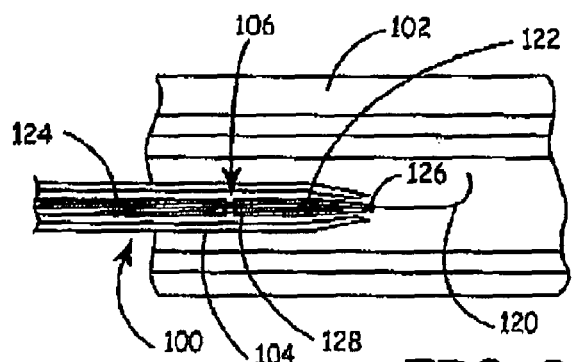
FIG. 2A is a schematic view of an embolism protection device within a sheath being delivered in a patient's vessel.
Figure 2B:
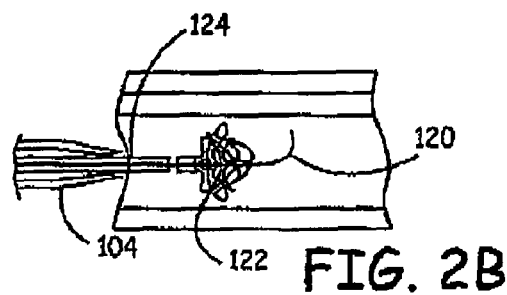
FIG. 2B is a schematic view of the device of FIG. 2A with the sheath drawn back.
Figure 2C:
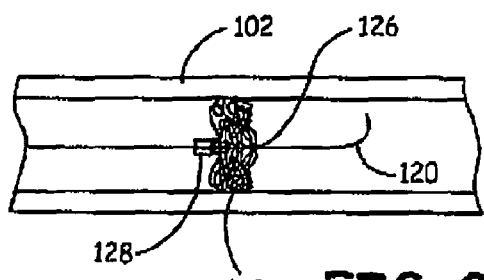
FIG. 2C is a schematic sectional view of the embolism protection device of FIG. 2A deployed off a guide wire.
Figure 2D:
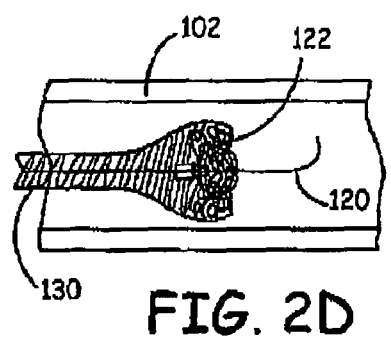
FIG. 2D is a schematic view of the device of FIG. 2C being removed through a retraction device.

As used herein, SCF fibers refer broadly to fibers having channels or capillaries along the surface running generally along the length of the fiber or a portion thereof. Fibers have their usual meaning as structures with a length that is significantly larger than the dimensions along a cross section perpendicular to the length. The capillaries can run along substantially the entire length or a fraction thereof. Due to the presence of the capillaries, a cross section through the fiber at the capillary(ies) has a shape with an edge having changing curvatures. A suitable cross sectional shape is shown schematically in FIG. 1A, although any of wide range of cross sectional shapes are suitable as long as a surface capillary is formed. As shown schematically in FIG. 1A, the fiber has eight surface capillaries. For comparison, a fiber without surface capillaries is shown schematically in FIG. 1B at the same magnification as the fiber in Fig. 1A having roughly the same surface area as the fiber in Fig. 1A. The surface capillary fiber a surface area that is at least about a factor of 1.5 greater than a corresponding circular fiber with an equivalent diameter.

SCF fibers for use in the medical devices are generally formed from biocompatible polymers. SCF fibers can be fabricated from synthetic polymers as well as purified biological polymers and combinations thereof. Suitable synthetic polymers include, for example, polyamides (e.g., nylon), polyesters (e.g., polyethylene teraphthalate), polyacetals/polyketals, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers. Based on experience in the medical field, suitable resorbable polymers include, in particulaar, polylactic acid, polyglycolic acid, and copolymers and mixtures thereof.

Appropriate polymers also include biological polymers. Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers generally are bioresorbable. Purified biological polymers can be appropriately formed into a polymer material for further processing into fibers.

A suitable length of the fibers generally depends on the specific use of the fiber. In a broad sense, the fibers generally range in size from about 500 microns to about 10 centimeters in length, although lengths outside this range are also contemplated. Also, in general, fibers have a large aspect ratio, which is the ratio of the length of the fiber to its width, with a value typically of at least about 3. Aspect ratios can be at least about 10 in some embodiments, in further embodiments at least about 100, in other embodiments at least about 1000, and in additional embodiments from about 2000 to about 10,000. Similarly, the capillaries generally have a length along the fiber length that is at least a factor of three greater than the width of the capillary. In some embodiments, the surface capillaries extend along at least about 5 percent of the fiber length, in further embodiments at least about 20 percent, in further embodiments at least about 40 percent and in other embodiments at least about 60 percent. In some embodiments, the surface capillaries extend substantially along the entire length of the fiber. A person of ordinary skill in the art will recognize that additional ranges of fiber length, aspect ratio and capillary channel extent are contemplated and are within the present disclosure. In particular, one or both ends of the fiber may have different properties or no surface capillaries in some embodiments.

The properties of the surface channels and the corresponding cross-section of the fiber generally depends on the process used to form the fibers. U.S. Pat. No. 4,842,792 to Bagrodia et al., entitled "Drafting Process For Preparing A Modified Polyester Fiber," incorporated herein by reference, describes one approach for forming a fiber with a continuous surface "groove" that runs along the length of the fiber. The process in the '792 patent forms the groove starting from a conventional fiber. Another form of shaped fibers is described in U.S. Pat. No. 5,277,976 to Hogle et al., entitled "Oriented Profile Fibers," incorporated herein by reference. Other shaped fibers notches or channels are described in U.S. Pat. No. 5,458,963 to Meirowitz et al., entitled "Nonwoven Web Containing Shaped Fibers," incorporated herein by reference. Fiber with fairly complex surface channel geometry are described in U.S. Pat. No. 5,972,505 to Phillips et al., entitled "Fibers Capable Of Spontaneously Transporting Fluids," incorporated herein by reference. A further approach for forming a fiber with surface capillaries is described in U.S. Pat. No. 5,200,248 to Thompson et al. (hereinafter the '248 patent), entitled "Open Capillary Channel Structures, Improved Process For Making Capillary Channel Structures, And Extrusion Die For Use Therein," incorporated herein by reference. The Background section of the '248 patent additionally references a variety of alternative embodiments of approaches for forming fibers with surface channels or capillaries. Any of these approaches can be used. However, the fibers formed by the process of the '248 patent itself have desirable characteristics and versatility.

Since suitable fibers can be formed in a variety of ways, the cross sectional properties of the fibers can have similar variety. In general, the cross sectional properties of the fibers are relatively uniform along the length of the capillaries, although such a property is not needed in some embodiment for desirable function. The cross sectional properties can be considered as an average of the cross section along the length of the fiber with the surface capillaries. Due to the presence of at least one surface capillary, the outer contour of the cross section has at least one change in curvature. In some embodiments, the fiber has a plurality of surface capillaries with corresponding changes in curvature. Thus, a fiber can have a single surface capillary, two surface capillaries, or in appropriate embodiments 3-25 surface capillaries as well as any and all values within this range. For example, the cross section has an outer perimeter that is formed by tracing along the outer surface of the cross section.

The cross section can be characterized by a circumference that can be determined by magnifying the cross section, conceptually wrapping a tight string around the circumference, measuring the length of the conceptual string and scaling the length back according to the inverse of the magnification to obtain the circumference. Similarly, the area mapped out with this virtual string also characterizes the cross section of the fiber. The radius of the fiber can be estimated from the circumference if an overall circular shape is assumed since the circumference, c, can be related roughly to a radius, r, by the formula $c = 2\pi r$. The capillaries themselves can be characterized roughly by their number, shape and wall thickness between the capillaries. Suitable wall thickness can depend on the size of the capillaries as well as the overall thickness of the fiber.

As with the fiber length, the thickness of the fibers can be selected appropriately for the particular use of the fiber. Fiber thickness can be measures in several ways. As described in the previous paragraph, the radius of the fiber can be roughly estimated from the assumption of a circular cross section. Alternatively, one can define an average diameter by taking an average cross section and then averaging the length of segments through the center of the cross section that intersect the circumference of the cross section. Also, calipers can be used to measure thickness, which can be averaged to obtain a value of the diameter. These various approaches at estimating the radius or diameter generally give values of roughly the same magnitude. Also, in the fiber field, a pragmatic way has been developed to characterize fiber thickness without the need to resort to magnification of the fibers. Thus, fiber thickness can be measured in units of denier. Deniers correspond to the number of grams per 9,000 meters of yarn with a larger value corresponding to a thicker fiber. In some embodiments, suitable fibers have diameters from 50 microns to about 5 millimeter, in further embodiments from about 100 microns to about 2 millimeters, and in additional embodiments from about 150 microns to about 1 millimeter. As measured in denier, SCF fibers can have sizes ranging from about 1.5 denier to about 1000 denier in size, in additional embodiments from about 5 denier to about 500 denier, in other embodiments from about 10 denier to about 250 denier and in further embodiments from about 20 denier to about 200 denier. A person of ordinary skill in the art will recognize that additional ranges of fiber thickness in diameter measurements or in denier are contemplated and are within the present disclosure.

A capillary channel can have a width suitable for the particular application based on its function and its interaction with associated fluids. For many applications of interest, suitable capillary widths range from about 1 micron to about 0.5 mm (500 microns), in other embodiments from about 5 microns to about 250 microns, in further embodiments from about 10 microns to about 200 microns and in additional embodiments from about 25 microns to about 100 microns as well as all ranges and subranges within these. The width of a capillary channel can be evaluated from a measurement on a micrograph of fiber cross section based on the magnification. The width can be taken as the distance between the edges of the capillary along the circumference of the fiber such that the width corresponds with the surface opening of the capillary. A person of ordinary skill in the art will recognize that additional ranges of values of capillary widths within the explicit ranges are contemplated and are within the present disclosure.

Further characterization of the fibers can barrow from the approaches outlined in the '248 patent. In particular, the overall capillary sizes can be characterized. In some embodiments of interest, the fibers have a specific capillary volume of at least about 0.5 cc/g, in other embodiments at least about 1.0 cc/g, in further embodiments at least about 2.0 cc/g and in additional embodiments at least about 3.0 cc/g. Also, the specific capillary surface area can be at least about 500 cm$^2$/g, in some embodiments at least about 1000 cm$^2$/g, in further embodiments at least about 2000 cm$^2$/g, and in other embodiments at least about 3000 cm$^2$/g. A person of ordinary skill in the art will recognize that additional ranges of capillary volumes and capillary surface areas are contemplated and are within the present disclosure. Tests for evaluating these values are summarized below.

In some embodiments, it is desirable for aqueous liquid, such as bodily fluids or components thereof to enter the capillaries. For these embodiments, the polymer properties and the capillary properties can be selected appropriately such that the capillaries can accept the liquid accounting for the surface tension of the liquid and the chemical properties of the liquid and the fiber. In particular, it can be desirable to provide for aqueous liquid entry into the capillaries for embodiments involving removal of particulates from a bodily fluid and for embodiments involving transport of biological liquids through the channels. Thus, relatively hydrophilic polymers, such as polyesters, generally are suitable fiber materials for incorporating aqueous liquids into the capillaries.

While various capillary structures are covered herein, in some embodiments with high capillary volumes, the capillary walls can be particularly thin. If the capillary walls are thin, the capillary can collapse under compressive forces unless the polymer is resistant to compressive strain. Thus, in some embodiments, it is desirable for the polymers to have a modulus of elasticity of at least about 100 MPa and in other embodiments at least about 750 MPa at biological temperatures from about 35° C. to about 40° C. Similarly, the wetting properties of the polymer can be relevant. In some embodiments, the polymer has an adhesion tension with distilled water of at least about 20 dynes/cm and in further embodiments at least about 25 dynes/cm. With respect to the resulting capillary properties, the capillary structures in some embodiments exhibit a capillary sorption of at least about 1.5 cc/g at 5.0 cm capillary suction/hydrostatic tension with distilled water, in other embodiments at least about 4 cc/g at 5.0 cm and in further embodiments at least about 4 cc/g at 10 cm capillary suction. The test for capillary sorption is described below. A person of ordinary skill in the art will recognize that additional ranges of modulus of elasticity, adhesion tension, and capillary sorption within the explicit ranges are contemplated and are within the present disclosure.

Test methods for evaluating the specific capillary volume, the specific surface capillary area and the adhesion tension are described in detail in the '248 patent, which is incorporated herein by reference for the explicit description of the determination of these values.

In general, the fibers can be attached together for incorporating into a device. For example, the fibers can be attached using chemical crosslinking, adhesives, twisting, weaving, heat bonding, or the like or combinations thereof. Chemical crosslinking can involve the use of radiation or the like to active the polymer to form chemical crosslinks and/or crosslinking agents that can bond with two or more polymer fiber elements. Suitable adhesives for bonding the fibers or a portion thereof are described in detail below. The fibers can be twisted or braided, for example using conventional approaches, to form Weaving or similar physical association can be used to form structures for use in the device. In general, if formed form appropriate polymers, fibers or portions thereof can be associated together using heat bonding, which can be controlled to form desired fusing without inducing an undesirable loss of the fiber and surface channel structure. Furthermore, the fibers can be associated with additional materials or the like within the device to secure the fibers and or form the device, as described further below.

Other Materials

In addition to the SCF fibers, the medical devices can comprise one or more additional materials. These materials may be used to interface with the SCF fibers appropriately for the specific desired function of the fibers or for other purposes related to the medical device structure and/or function. Suitable additional materials may or may not be biocompatible. However, additional biocompatible materials can be used with respect to portions of the device that contact bodily fluids. Suitable additional materials can be, for example, polymers, metals, ceramics, bioactive compounds, tissue, and the like. Bioactive compounds are described further below.

Any non-biocompatible materials can be used for manipulating and/or structurally supporting the portion of the device that contacts bodily fluids. For example, for example, various materials, such as conventional structural materials, can be used to form the structural and control portions of an extra-corporeal apparatus. For example, embodiments of a dialysis apparatus are described further, for example, in U.S. Pat. No. 5,722,947 to Jeppsson et al., entitled "Apparatus For Carrying Out Peritoneal Dialyses," incorporated herein by reference. Features of the dialysis apparatus can be adapted for other applications involving extra-corporeal manipulation of bodily fluids. Similarly, various control apparatus can be used for manipulating a catheter or the like in conjunction with certain percutaneous appartuses. Catheter apparatuses are described further, for example, in U.S. Pat. No. 6,176,843 to DiCaprio et al., entitled "Catheter With Distal Manifold Prep Valve/Manifold," incorporated herein by reference.

With respect to suitable biocompatible materials appropriate ceramics include, without limitation, hydroxyapatite, alumina and pyrolytic carbon. Biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, and Nitinol®, a nickel-titanium alloy. Additional materials, such as metals, can be introduced into a polymer component to render the portion of the device radio-opaque such that it can be visualized via angiography or clinical techniques. Generally, suitable metals comprise biocompatible metals. Guide wires, tethers and the like can also be formed from these biocompatible metals and/or biocompatible polymers, which can be formed from the same materials as the biocompatible fabrics described below.

Also, the embolism protection device can further comprise a biocompatible adhesive, such as on the exterior of the device to facilitate anchoring of the device at the place of delivery within a patient or within the device to secure portions of the device together. In some embodiments, a biocompatible adhesive is used to secure together portions or components of the device. In additional or alternative embodiments, the SCF fibers are used to deliver a medical adhesive. In addition, a medical adhesive can be combined with a bioactive agent and placed within the surface capillaries to deliver the bioactive agent with selected deliver based on the character of the adhesive, which can be a resorbable adhesive. Particular medical adhesives are described further in a subsequent section.

As noted above, components of the medical device can be formed from polymers. The character of the appropriate polymers generally depends on the particular use of the component. In some embodiments, the polymers are elastic or flexible polymers, while in other embodiments the polymers are rigid polymers that can be used to form structural components. In general, for components that do not contact bodily fluids and polymers with desired properties can be used, such as commercially available polymer. For components that contact bodily fluids a variety of biocompatible polymers can be adapted for use. Suitable flexible polymers include, for example, polyurethanes, polydimethyl siloxane, polytetrafluoroethylene and copolymes and mixtrues thereof. Suitable rigid polymers include, for example, polyacetals, such as Delrin® and Celcon®, polysulfones, polyethersulfones, polyarylsulfones, polyetherether-ketones, polyetherimides and copolymers and mixtures thereof. In some embodiments, it is desirable to use a resorbable polymer, such as, dextran, hydroxyethyl starch, derivatives of gelatine, polyvinylpyrrolidone, poly[N-(2-hydroxylpropyl) methacrylamide], polyglycols, polyesters, poly (orthoesters), poly(ester amides), polyanhydrides and copolymers and mixtures thereof. Resorbable polyesters include, for example, poly (hydroxy acids) and copolymers thereof, poly(epsilon-caprolactone), poly (dimethyl glycolic acid), poly (hydroxy butyrate) and copolymers and mixtures thereof. Other resorbable polymers include, for example, D, L-polylactic acid, L-polylactic acid, poly(glycolic acid), and copolymers of L-lactic acid, D-lactic acid and glycolic acid.

Also, portions of the device, such as portions that contact a patient's bodily fluids, can be covered with a biocompatible fabric. Biocompatible fabrics can be formed from a variety of biocompatible materials, such as silk, nylon and/or polyesters, including, for example, Dacron® polyester. The fabric may or may not be formed from the SCF fibers, such as by weaving. Furthermore, the fabric may or may not be woven. The fabric can be selected to have an appropriate porosity for the desired use of the material. For example, if the fabric is formed from SCF fibers, the pore sizes can be selected to provide for flow around the fibers. For nonwoven fabrics, a desired porosity can be introduced by mechanically puncturing the fabric with a fine needle or the like or by laser drilling appropriate pores. A wide variety of lasers with moderate power can be used for the drilling and conventional optics can be used to focus the laser beam to produce the desired pore size.

The polymer components can be prepared by any of a variety of approaches including, for example, conventional polymer processing methods. Suitable approaches include, for example, injection molding, which is suitable for the production of polymer components with significant structural features, and rapid prototyping approaches, such as reaction injection molding and stereo-lithography.

Other embodiments could employ surfactants or other surface finishes, as constituents for the medical device, which can modulate fluid management or biological rejection to the device. Also, other embodiments may entail modulation of these coatings to produce either a hyroholicity or hydrophobic nature to the materials.

In some embodiments, the medical device comprises a tissue material. Appropriate tissue materials can be formed from natural materials, synthetic tissue matrices and combinations thereof. Synthetic tissue matrices can be formed from extracellular matrix proteins that are crosslinked to form a tissue matrix. Extracellular matrix proteins are commercially available. Natural, i.e. biological, tissue material for use in the invention includes relatively intact tissue as well as decellularized tissue. These tissues may be obtained from, for example, native heart valves, portions of native heart valves such as roots, walls and leaflets, pericardial tissues such as pericardial patches, connective tissues, bypass grafts, tendons, ligaments, skin patches, blood vessels, cartilage, dura mater, skin, bone, fascia, submucosa, umbilical tissues, and the like.

Natural tissues can be derived from a particular animal species, typically mammalian, such as human, bovine, porcine, canine, seal or kangaroo. These tissues may comprise a whole organ, including homografts and autografts. These natural tissues generally include collagen-containing material. Natural tissue is typically, but not necessarily, soft tissue. The tissue can be decellularized. Decellularization approaches are described, for example, U.S. Pat. No. 5,855,620 to Bishopric et al., entitled "Matrix Substrate for a Viable Body Tissue-Derived Prosthesis and Method for Making the Same," incorporated herein by reference.

Tissues can be fixed by crosslinking. Fixation provides mechanical stabilization, for example, by preventing enzymatic degradation of the tissue. Glutaraldehyde, formaldehyde or a combination thereof is typically used for fixation, but other fixatives can be used, such as epoxides and other difunctional aldehydes. Aldehyde functional groups are highly reactive with amine groups in proteins, such as collagen. Treatment of aldehyde crosslinked tissue to moderate toxicity effects of crosslinking is described further in U.S. Pat. No. 6,471,723 to Ashworth et al, entitled "Biocompatible Prosthetic Tissue," incorporated herein by reference.

Bioactive Agents

The medical devices or components thereof generally provide mechanical and structural functions within the patient. However, it may be desirable to combine the mechanical features of the device with biologically active agents to provide another dimension to the treatment.

In some embodiments the association of bioactive agents with the device can provide treatment to shrink or eliminate emboli, such as within an embolic protection device, and/or to deliver a bioactive agent in the vicinity of and/or downstream from the device. Suitable bioactive agents include, for example, thrombolytic (anti-thrombogenic) agents, anti-platelet agents, anti-coagulation agents, anitmicrobial agents, vascular-dilators, pro-coagulation agents, restenosis inhibitors, acidic agents, growth factors and combinations thereof.

Suitable thrombolytic agents include, for example, tissue-type plasminogen activator (tPA), mutated forms of tPA, such as TNK-tPA and YM866, urokinase, streptokinase, staphylokinase, and the like. In particular; tPA is a polypeptide that acts upon plasminogen to form. plasmin. Plasmin breaks down fibrin, one of the main structural proteins in blood clots. Plasmin also lyses fibrinogen, a precursor of fibrin. tPA can be produced according to the method described in U.S. Pat. No. 4,935,368 to Ryotaro et at, entitled "Process For Producing Tissue Plasminogen. Activator," incorporated herein by reference. An effective precursor of tPA is described in U.S. Pat. No. 6,001,355 to Dowdle, entitled "Pro-tPA For The Treatment Of Thrombosis, Embolism And Related Conditions," incorporated herein by reference. Analogs, e.g., mutated forms, of tPA are known, for example, as are described in U.S. Pat. No. 5,106,741 to Marotti et al., entitled "Tissue Plasminogen Activator (TPA) Analogs," PCT published application WO 93/20194 to Sato et a., entitled "TPA Analog," and PCT published application WO 02/22832 to Xia et al., entitled "A Cell Line Expressing Mutated Human Tissue-Type Plasminogen Activator, The Constructing Strategy Thereof And Methods Of Preparing Expressed Protein," all three of which are incorporated herein by reference. Elsewhere in this application including the claims, tPA refers to natural tPA, fragments thereof and analogs thereof that are effective to stimulate the formation of plasmin.

Together with an appropriate materials design, a desirable medical device associated with tPA can be capable of destroying or shrinking emboli associated with cardiopulmonary bypass. Recent reports suggest that most of the emboli generated during cardiopulmonary bypass have a significant fibrin component. The body's primary means of degrading fibrin is via tissue plasminogen activator (tPA). tPA is currently in clinical use as a remedy for heart attack and stroke (thrombolysis, reperfusion therapy). This therapy involves delivering tPA through an intravenous line to break up and dissolve a clots in the coronary artery, thereby restoring blood flow. tPA is of particular interest for use with medical devices described herein for providing protection against emboli or the like, based on the high specificity of tPA for clot degradation without causing systemic bleeding events.

Suitable anti-platelet agents include, for example, acetylsalicylic acid, ADP inhibitors, phosphodiesterase III inhibitors, glycoprotein IIB/IIIA inhibitors, adenosine reuptake inhibitors, nitrates, such as nitroglicerin and isosorbide dinitrate, and Vitamin E. Suitable anti-coagulation agents include, for example, heparin, warfarin, and the like. Suitable growth factors include, for example, vascular endothelial growth factor (VEGF) and the like. Generally, suitable forms of these agents are readily available commercially.

In some embodiments, materials are incorporated into the device that form by decomposition a therapeutic composition. For example, nitric oxide (NO) can stimulate beneficial vascular responses. Compounds with an $NONO^-$ functional group can emit nitric oxide following implantation of the medical device. Suitable compositions include, for example, $(CH_3)_2CHNHNONO^-$, $(CH_3CH_2)_2NNONO^-$, $H_2N(CH_2)_3NHNONO^-$, $NaNONONa$. The synthesis of 1-(2S-carboxypyrrolidin-1-yl)-oxo-2-hydroxydiazene disodium salt, 1-hydroxy-2-oxo-3-carboxymethyl-3-methyl-1-triazine N-methylamide disodium salt, 1-hydroxy-2-oxo-3-carboxymethyl-3-methyl-1-triazine N-methylamide sodium salt, the bis(nitric oxide) adduct of L-prolyl-L-leucylglycinamide, and corresponding protein adducts are described in U.S. Pat. No. 5,632,981 to Saavedra et al., entitled "Biopolymer-Bound Nitric Oxide Releasing Compositions, Pharmaceutical Compositions Incorporating Same And Methods Of Treating Biological Disorders Using Same," incorporated herein by reference. Conjugates of heparain, for example with dermatan sulfate, that are effective to prevent thrombosis are described in U.S. Pat. No. 6,491,965 to Berry et al., entitled "Medical Device Comprising Glucosaminoglycan-Antithrombin III/Heparin Cofactor II Conjugates," incorporated herein by reference. Furthermore, some polymers decompose to form an acidic moiety, such as polyhydroxybutyrate degrading to 3-hydroxyvaleric acid. Such acidic agents can retard emboli formation in the vicinity of its release.

In some embodiments pro-coagulation agents may be used. These agents include metals, biological agents or other energetic stimuli. An example of a metal compound is silver nitrate (styptic pencils), which can be used to stem blood flow significant wounds. Other biological materials can be produce similar results, for example, collagen or another protein or combination of proteins associated with the coagulation cascade i.e. factor VIIa, Xa, V, XIIIa, Fibrin, Thrombin, von Willepbrand factor (vWF) or other co-clotting factors secreted by platelets or bound from plasma. These agents are meant as examples and are not limiting.

In some embodiments blood clotting may be not advantageous and elution-of agents to prevent clot formation may be useful. This can be preformed by associating the medical article with bioactive agents that inhibit or reveres the thrombolytic process, i.e. Heparin Sulfate, Antithrombin II, Protein C, and Tissue Plasminogen Activator.

In other embodiments, the association of anti-microbial agents to help prevent and or treat potential infections associated with medical articles. These agents include with out limitation antibiotics, anti-microbial metals. Examples of antibiotics include, for example, penicillin, phosphonomycin, bacitracin and vancomycin, which interfere with cell wall synthesis. In particular, penicillin inhibits a crosslinking reaction in cell wall synthesis. Other antibiotics, such as streptomycin, tetracycline, chloramphenicol and erythromycin, act by inhibiting protein synthesis by binding to bacterial ribosomes. Other suitable antibiotics include, for example, bacteriocins, such as lysostaphin, and peptide antibiotics, such as actinomycin, bacitracin, circulin, fungisporin, gramicidin S, malformin, mycobacilin, polymyxin, tyrocidine and valinomycin.

In other embodiments delivery of bioactive agents to inhibit restenosis of vascular vessels may be desirable. Suitable therapeutic agents to inhibit restenosis include, for example, radioactive atoms/ions, nitric oxide releasing agents, heparin, angiopeptin, calcium channel blockers, angiotensin converting enzyme inhibitors, cyclosporin A, trapidil, terbinafine, colchicine, taxol, c-myc and c-myb antisense, antibodies to SMC mitogen platelet derived growth factor, and the like.

Combinations of two or more bioactive agents of the same class and/or of different classes can be used.

The bioactive agent can be associated with the materials of the embolism protection device by one or more approaches. For example, the device can be contacted with a solution of the agent such that the agent can be infused within the device. The agent is then released, possibly gradually, upon implantation of the device. In other embodiments, the bioactive agents are placed in contact with the polymers during the polymerization and/or crosslinking/grafting steps such that the bioactive agents are incorporated within the polymer matrix. The bioactive agents then elute following implantation. In particular, SCF fibers can take in liquid compositions within the surface capillaries at relatively large volumes for subsequent elution of the composition following delivery of the device. The bioactive agents can be adsorbed into the capillary channels along with a biocompatible adhesive or other control release agent. Elution of the bioactive agent from the adhesive or degradation of the adhesive can release the bioactive agent in a controlled way.

For systemic administration, the therapeutic dose of tPA for a human patient can be 0.01 to 80 micro moles (70-8750 ng/ml) but is thought to be most effective at 500-1000 ng/ml. See, for example, Wu JH and Diamond SL, "Tissue plasminogen activator (tPA) inhibits plasmin degradation of fibrin. A mechanism that slows tPA-mediated fibinolysis but does not require alpha 2-anitplasmin or leakage of intrinsic plasminogen," Journal Clinical Investigation 1995; 95(6):2483-2490. Lower doses may be effective with local delivery since the local concentration can be higher over the delivery period. An appropriate corresponding dose for local delivery can be sustained throughout the time of implant. If the dose is released too quickly, a toxic environment can ensue (>25,000 ng/ml for systemic delivery). See, for example, Hrach CJ, Johnson MW, Hassan AS, Lei B. Sieving PA and Elner VM, "Retinal toxicity of commercial intravitreal tissue plasminogen activator solution in cat eyes," Archive Opthalmology 2000 May; 118(5): 659-63. To determine the initial loading dose, the release kinetics of tPA from the device can be used to deliver a desired dose of tPA or other biologically active agent. An empirical evaluation of an appropriate dose can be estimated from in vitro studies, such as the flow loop studies described in copending U.S. patent application Ser. No. 10/414,909 now U.S. Pat. No. 7,303,575 to Ogle, entitled "Embolism Protection Devices," incorporated herein by reference, or from animal studies. In some embodiments, it may be desirable to deliver the biologically active agent with a suitable biocompatible carrier. Suitable biocompatible carriers can be, for example, a physiologically buffered saline. Suitable buffers can be based on, for example, the following compounds: phosphate, borate, bicarbonate, carbonate, cacodylate, citrate, and other organic buffers. such as tris (hydroxymethyl)aminomethane (TRIS), N-(2-hydroxyethyl) piparazine-N'-(2-ethanesulfonic acid) (HEPES) or morpholine propanesulphonic acid (MOPS). The ionic strength of the biocompatible carrier can be adjusted by the addition of one or more inert salts including, for example, NaCl, KCl and combinations thereof. In some embodiments, the ionic strength is near physiological values.

Additionally or alternatively, genes coding for desired polypeptide-bioactive agents can be delivered in a vector. The vector can be taken up by adjacent cells and expressed as the protein. Suitable vectors are known in the art, and include, for example, viral vectors, plasmids and the like. In particular, a vector encoding tPA can be delivered through the device. The effectiveness of a vector for tPA expression in rabbits is described further in Waugh et al., "Gene therapy to promote thromboresistance: Local over-expression of tissue plasminogen activator to prevent arterial thrombosis in an in vivo rabbit model," Proceeding of the National Academy of Sciences-USA 96(3): 1065-1070 (Feb. 2, 1999), incorporated herein by reference. Vectors, for example, plasmids and viral vectors, suitable for transforming human cells with appropriate control sequences for expression in human cells are described further in U.S. Pat. No. 5,106,741 to Marotti et al., entitled "Tissue Plasminogen Activator (TPA) Analogs," and U.S. Pat. No. 4,935,368 to Ryotaro et al., entitled "Process For Producing Tissue Plasminogen Activator," both of which are incorporated herein by reference.

Medical Adhesives

Other embodiments relate to the use of medical adhesives in combination with medical devices comprising SCF fibers. A medical adhesive can be used advantageously in several different roles within these devices. Medical adhesives have the advantage that they are suitable for contacting bodily fluids. With respect to these devices, the medical adhesive can be used to facilitate anchoring the device, the adhesive can be used in conjunction with the delivery of a bioactive agent, the adhesive can be used to hold together a portion of the medical device in a structural way and/or a medical adhesive can be delivered to a selected location through the surface capillaries of the fiber. For convenience, adhesive, as used herein, refer generally to the adhesive in a form for application as well as the adhesive composition following curing in a set form.

Appropriate medical adhesives should be biocompatible, in that they are non-toxic, non-carcinogenic and do not induce hemolysis or an immunological response. In general, the adhesive can be a single component adhesive or multi-component adhesive. Further suitable adhesives include synthetic adhesives, natural adhesives and combinations thereof. For example, suitable biocompatible adhesives include commercially available surgical adhesives, such as cyanoacralate (such as 2-octyl cyanoacrylate, Dermabond™, from Ethicon Products), fibrin glue (such as Tissucol® from Baxter) and mixtures thereof, although a wide range of suitable adhesives are discussed further below.

The following is a list of suitable synthetic adhesives, one component adhesives including, for example, cyanoacrylate compounds. Particular cyanoacrylates include, for example, methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, butyl-2-cyanoacrylate, fluorinated 2-cyanoacrylates and combinations thereof. Ethyl cyanoacrylate and butyl-2-cyanoacrylate are available from Loctite Corp., Hartford, Conn. These compounds harden quickly upon exposure to atmospheric humidity. The adhesive should be stored properly to avoid premature hardening.

Suitable two-component synthetic adhesives include, for example, urethane-based polymers, copolymers, and mixtures thereof. Polyurethanes are ester-amide derivatives of carboxylic acids. Urethane oligomers/prepolymers can be formed with terminal reactive functional groups. Because of the terminal functional groups, the prepolymers are particularly suitable for the formation of crosslinked mixed polymers exhibiting a range of desirable properties generally characteristic of polyurethanes and of the other components. With respect to the formation of an adhesive, in certain embodiments, the urethane prepolymer can be used as one component of the adhesive, with a crosslinking agent or agents being the other component or components of the adhesive.

Isocyanate (—NCO)—terminated urethane prepolymers are particularly suitable adhesive components. Polyurethanes including polyurethane prepolymers (urethane oligomers) can be formed either by the reaction of bischloroformates with diamines or the reaction of diisocyanates with polyhydroxy compounds. The approach to urethane polymerization involving diisocyanates with polyhydroxy compounds can be used to produce urethane prepolymers with isocyanate functional groups at their terminus. Suitable urethane prepolymers can be formed by the reaction of polyisocyanates with polyols.

Suitable polyisocynates include, for example, aromatic polyisocyanates containing 6-20 carbon atoms excluding the —NCO groups, such as o-, m- and p-phenylene diisocyanates (PDI), 2,4- and 2,6-tolulene d-socyanates (TDI), diphenylmethane-2,4' and 4,4'-diisocyanates, diphenylmethane 2-4'- and 4,4'-diisocyanates (MDI), naphthalene-1,5-diisocyanate, triphenylmethane 4,4',4"-trilsocyanate, polymethylenepolyphenylenepolyisocyanates (PAPI) obtained by phosgenation of aniline-formaldehyde condensation products, m- and p-isocyanato-phenyl sulfonyl isocyanate, and the like; aliphatic polyisocyanates containing 2-18 carbon atoms, such as ethylenediisocyanate; alicyclic polyisocyanates containing 4-15 carbon atoms, such as isophorone diisocyanate; araliphatic polyisocyanates containing 8-15 carbon atoms, such as xylylene diisocyanates; and modified polyisocyanates of these polyisocyanates, containing urethane, carbodiimide, allophanate, urea, biuret, urethdione, urethimine, isocyanurate and/or oxaolidong groups, such as urethane-modified TDI, carbodiimide-modified MDI, urethane modified MDI, and the like; as well as mixtures thereof.

For surgical adhesives, suitable polyisocyanates from this group include aromatic diisocyanates, particularly PDI, TDI (along with 2,4-and 2,6-isomers and mixtures of isomers with TDI), MDI (along with 4,4'- and 2,4'-isomers and mixtures isomers with MDI or PAPI), and modified polyisocyanates containing urethane, carbodiimide, allophanate, urea, biuret and/or isocyanurate groups, derived from PDI, TDI and/or MDI. Due to low toxicity, p-PDI (hereinafter PPDI) is particularly appropriate. Alternative embodiments include combinations of PPDI with a minor amount (usually up to about 500 by weight, and in some embodiments up to about 30% by weight) of one or more other polyisocyanates, such as aromatic polyisocyanates, particularly TDI, MDI, modified MDI and mixtures thereof.

Suitable polyols for the formation of the prepolymers include hydrophilic polyether polyols, other polyols and mixtures thereof. Representative suitable hydrophilic polyether polyols include adducts of ethylene oxide (hereinafter EO) or combinations of EO with other alkaline oxide(s) (hereinafter AO) formed with one or more compounds containing at least two active hydrogen atoms, such as polyhydric alcohols, polyhydric phenols, amines, polycarboxylic acids, phosphorous acids and the like. Suitable polyhydric alcohols include dihydric alcohols, such as ethylene glycol, trihydric alcohols, such as glycerol, and polyhydric alcohols having 4-8 or more hydroxyl groups, such as pentaerythritol. Representative suitable polyhydric phenols include mono- and poly-nuclear phenols, such as hydroquinone. Suitable amines for the formation of polyether polyols include ammonia, alkanol amines, such as mono-, di- and tri-ethanol amines, aliphatic, aromatic, araliphatic and alicyclic monoamines, aliphatic, aromatic, araliphatic and alicylic polyamines, and heterocyclic polyamines.

For the formation of urethane prepolymers, addition of EO, or a combination of EO with an AO, to active hydrogen atom-containing compounds can be performed in conventional ways, with or without catalysts, such as alkaline catalysts, amine catalysts and acidic catalysts, under atmospheric pressure or at an elevated pressure, in a single step or in multiple steps. Addition of EO and AO may be performed by random-addition, block-addition or combination thereof, such as random-addition followed by block-addition. Random-addition is a suitable approach.

Suitable polyols for producing NCO-terminated urethane prepolymers can have an average equivalent weight from about 100 to about 5,000, in some embodiments from about 200 to about 3,000 and generally 2-8 hydroxyl groups, or alternatively 2-4 hydroxyl groups. A person of ordinary skill in the art will recognize that additional ranges of molecular weight and numbers of hydroxyl groups within the explicit ranges above are contemplated and are within the present disclosure.

The polyisocyanate and polyol can be mixed with a ratio of NCO/OH of about 1.5 to about 5.0 and more preferably from about 1.7 to about 3.0. The resulting prepolymers can have an NCO-content from about 1% to about 10% by weight and in some embodiments about 2% to about 8% by weight. Lower NCO-contents can result in a low binding strength and higher NCO-contents can lead to brittle bonds. A person of ordinary skill in the art will recognize that additional ranges of functional group ratios and functional group weights within the explicit ranges are contemplated and are within the present disclosure.

The polyisocyanates and polyols react to form urethane prepolymers. These prepolymers are moderate molecular weight oligomers. The size of the oligomers is controlled by the relative amounts of NCO functional groups and OH functional groups. Since the NCO functional groups are added in excess, the polymerization terminates when all of the OH groups have reacted. The unreacted NCO groups form the basis for further polymerization to form the final adhesive. Bioresorbable urethane based adhesives can be made from suitable hydrophilic urethane prepolymers.

Suitable compositions for the second component of the urethane based medical adhesives include polyols, such as the polyols used to form the prepolymer. The amount of polyols added can be based on the number of functional groups remaining unreacted in the urethane prepolymer. Alternatively, the second component of the urethane oligomer adhesive can be an unsaturated cyano compound containing a cyano group attached to a carbon atom involved in the polymerizable double bond, such as cyano acrylic acids and esters thereof. Examples of these unsaturated cyano compounds include, for example, cyanoacrylic acid, cyano methacrylic acid, methyl cyanoacrylic acid, methyl cyanomethacrylic acid, ethyl cyanoacrylic acid, ethyl cyanomethacrylic acid, isobutyl cyanoacrylic acid, isobutyl cyanomethacrylic acid, corresponding esters, acrylonitriles, methacrylonitriles, cyanoacrylonitriles, cyanomethacrylonitriles and mixtures thereof. Such adhesives are described in U.S. Pat. No. 4,740,534 to Matsuda et al., incorporated herein by reference. Mixtures of polyols and unsaturated cyano compounds can be used as the second or additional component(s) of the adhesive.

The urethane based adhesive composition generally comprises about 20 to about 90 percent by weight urethane prepolymer and in some embodiments about 30 to about 70 percent by weight urethane prepolymer. The ratio of urethane prepolymer to unsaturated cyano compound can be varied to achieve a desired flexibility. The use of a higher percentage of urethane prepolymer can results in an adhesive with greater flexibility. A catalyst can be added if desired. Urethane based medical adhesives are discussed further in published PCT application WO00/43050, entitled "Medical Adhesives," incorporated herein by reference.

Adhesives based on components that are natural compositions generally are based on inherent natural binding affinities and corresponding biological responses. Generally, one or more components of the adhesive are a protein or protein based compound. Protein is intended to be interpreted broadly in terms of any compound with a polypeptide (i.e., amino acid) component, and may include derivatives of natural proteins and polypeptides with additional covalently or non-covalently attached components, such as additional polypeptides, nucleotides, carbohydrates, and other organic or inorganic compounds. Protein components generally contain amino acids with side chains with functional groups useful for binding with the remaining adhesive components. Also, if the substrate is a crosslinked tissue, an adhesive component can replace functional groups that had been eliminated in the tissue substrate by reactions during the crosslinking process.

A type of biological adhesive is based on the protein fibrinogen. Fibrinogen, also known as factor I, is involved in natural blood clotting processes The protein thrombin removes one or two peptides from fibrinogen to form fibrin. Thrombin is also involved in the blood clotting process. A variety of fibrin adhesives have been based on the crosslinking of fibrin. Fibrin glues generally involve combinations of fibrinogen, thrombin and Factor XIII. Factor XIII also is involved in the natural wound healing mechanism. Factor XIII, also known as fibrin stabilizing factor, is activated by thrombin, and converts soluble fibrin to an insoluble clot. Fibrin adhesives polymerize and also covalently crosslink with collagen and other tissue components to form a liquid tight bond. The final amounts of the fibrinogen, thrombin or factor XIII components in the complete adhesive can be adjusted, as desired, to yield selected adhesive properties, such as strength and/or cure times, or for convenient application.

U.S. Pat. No. 4,818,291 to Iwatsuki et al., incorporated herein by reference, describes the inclusion of silk-fibroin protein into a fibrin glue to enhance its mechanical strength. Fibrin adhesives may also contain albumin, as described in U.S. Pat. No. 4,414,976 to Schwarz et al., incorporated herein by reference.

Another type of adhesive includes a biological component and a synthetic component. Generally, the biological component includes a protein. For example, gelatin-resorcinol aldehyde adhesives involve a gelatin-resorcinol material that is formed by heating gelatin and resorcinol. Gelatin is formed by hydrolytic activity on collagen protein. Formaldehyde, glutaraldehyde or the like can be used to crosslink the gelatin-resorcinol material to complete the formation of the glue.

A similar adhesive can be formed from water soluble proteinaceous material and di- or polyaldehydes. The proteinaceous materials may be purified proteins or mixtures of proteins. Suitable proteins include albumins, including ovalbumins. Proteins of particular interest include serum albumins of human or animal origin. Suitable water soluble di- or polyaldehydes include glyoxal and glutaraldehyde. The adhesive cures within a minute or less after the application of the aldehyde by spraying a layer over a coating of the proteinaceous material. Such adhesives are described further in U.S. Pat. No. 5,385,606 to Kowanko, incorporated herein by reference.

Similar adhesives based on proteinaceous material have been described in U.S. Pat. No. 5,583,114 to Barrows et al., incorporated herein by reference. Again, the proteinaceous material can include serum albumin as a primary component. The second component includes bifunctional crosslinking agents, with some crosslinking agents including polyethylene glycol with a molecular weight ranging from about 1,000 to about 15,000. The polyethylene glycol can be modified to incorporate leaving groups to activate the crosslinking agent to bind at primary or secondary amines of the proteins. Suitable leaving groups include, for example, succinimidyl, maleimidyl, phthamimidyl, other imides, heterocyclic leaving groups such as imidazolyl, aromatic leaving groups such as nitrophenyl, and fluorinated alkylsulfone leaving groups such as tresyl ($CF_3$—$CH_2SO_2$—O—). A linking group can be bonded between the polyethylene glycol and the leaving group.

The adhesives can contain additives to modify the mechanical properties of the adhesive. Suitable additives include, for example, fillers, softening agents and stabilizers. Representative fillers include, for example, carbon black and metal oxides, silicates, acrylic resin powder, and various ceramic powders. Representative softening agents include, for example, dibutyl phosphate, dioctylphosphate, tricresylphosphate, tributoxyethyl phosphates and other esters. Representative stabilizers for the urethane based polymers include, for example, trimethyldihydroquinone, phenyl-.beta.-naphthyl amine, p-isopropoxydiphenylamine, diphenyl-p-phenylene diamine, and the like. Protein based adhesives can also contain sugars such as glucose or sucrose to improve solubility, and stabilizers, including heparin. Fibrin glues can contain additional components, such as an inhibitor of fibrinolysis (anti-fibrolytic agents), for example, aprotinin and/or transexamic acid, with calcium chloride.

The properties of the adhesive generally are selected based on the particular application. In particular, the hardening rate and the adhesive strength can be selected based on the discussion above by a person of skill in the art. The adhesive for delivery may or may not comprise a liquid carrier. If the adhesive is applied to the medical device away from the body and cured and dried before contacting bodily fluids, the carrier may nit need to be biocompatible itself. However, for applications in which the carrier may contact bodily fluids, the carrier should also be biocompatible. Suitable biocompatible carriers include, for example, aqueous carriers such as purified water, buffer and/or saline. The biocompatible carrier generally is sterile.

With respect to forming a medical device with a medical adhesive, the adhesive can be applied using, for example, conventional manufacturing approaches. For example, a bundle of SCF fibers can be secured together with an adhesive. As an example, fibers can be arranged in an aligned bundle, and an adhesive can be used to secure the bundle together near an end of the bundle. Generally, the adhesive would be cured before use of the article. In general, adhesive can be used in any of a variety of roles for assembly of the medical device before use.

In some embodiments, a medical adhesive can be used to deliver a bioactive agent from SCF fibers. In general, methods to associate and deliver a biologically active agent, such as those described above, from SCF medical articles are numerous. For example, the agents may be released in a controlled fashion from the material by means known in the art. The SCF fiber structure provides unique advantages to accomplish a variety of treatment methods. The increased surfaces area of the capillaries increases additional surface for applying surface coatings with the bioactive agents. The grooves or surface capillaries can act to entrap the agents in their interstices (as liquid or solid). Or the SCF device material could be formulated with the bioactive agent entraped in polymeric formulation to diffuse out of the structure over time. The bioactive agent is combined with the polymer formulation prior to extrusion, molding or other approach to form the fiber. These delivery approaches can be practices alone or in combination. Other suitable techniques may employ creative new delivery techniques as gene therapy, microspheres, or polymeric temperature release. Local delivery of the bioactive agent can be directed to the specific sites without introducing larger systemic quantities of the agent. In some alternative embodiments, an agent is directly covalently bonded to the biocompatible material without the use of a binder matrix of an adhesive. In other embodiment, photochemical coupling can be used for covalent coupling. Photochemical coupling is based on the use of high energy light, e.g., ultraviolet light, to form reactive intermediates of certain functional groups. These reactive intermediates can form carbon-carbon bonds between two compositions.

For embodiments in which the bioactive agent is applied to a SCF fiber using an medical adhesive, the bioactive agent can be combined with a liquid adhesive composition which is contacted with the fibers. The liquid with the adhesive and bioactive agent can then adsorb into the surface capillaries. The large volume of the surface capillaries provides for the adsorption of a corresponding large volume of bioactive agent and adhesive. Once the adhesive cures, the mixture of bioactive agent and adhesive is secure within the surface capillaries. Upon delivery of the medical device, the bioactive agent can be delivered by extraction of the bioactive agent from the adhesive matrix and/or by resorption or degradation of the adhesive to release the bioactive agent. The selection of the adhesive properties can be used to adjust the delivery rate of the bioactive agent. Also, the ratio of adhesive to bioactive agent can similarly be used to adjust the delivery rate and total dose.

For the implantation within a pateint, a variety of approaches, such as suturing, stapling, clamping, adhering with adhesive and combinations thereof, can be used to secure a prosthesis. Selection of a particular approach can depend on the particular implantation procedure. For example, attachment of a surgical polyester patch (FIG. 3) to the lung requires good biocompatibility and good adhesion but the strength may not be the same that is necessary in patching an aorta. The SCF fiber grooves can create a capillary system to adsorb the adhesives, the increased surface area, which increases the adhesive to surface ratio, also the grooves provides for mechanical interlocking. Both these factors increase the adhesive strength and permanence of the bond.

Thus, while medical adhesives can be used for implantation of prostheses without associating the adhesive with SCF fibers, the combined association of the adhesive with SCF fibers for anchoring the medical device. In some embodiments, ends of a group of SCF fibers can be associated with an adhesive. Then, contacting the fiber ends with the adhesive to a structure within the patient, such as a tissue, a bond can be formed between the fiber ends and the tissue or other body portion. Alternatively, the fibers can be formed into a fiber structure, such as a mesh of woven or entangles fibers, and the fiber structure with an adhesive can form a strong bond between the fiber structure and a selected body portion. The fiber structure can be similarly attached to other portions of the medical device, for example, through an adhesive bond, chemical bonds and/or mechanical attachment.

Furthermore, SCF fibers, due to their ability to deliver significant quantities of liquid, can be used to deliver a quantity of adhesive in a controlled way to a selected location. In particular, a bundle of SCF fibers can be used for the controlled delivery of an adhesive formulation to a location from a reservoir of the adhesive. The SCF fiber bundle and the reservoir can be placed in the vicinity of delivery, for example through a catheter or the like. At an appropriate time, the reservoir can be punctured or otherwise opened to initiate flow from the reservoir to the SCF fibers. The capillary action of the fibers draws the adhesive composition into the surface capillaries. Contact with the other ends of the capillaries can draw the adhesive composition from the capillaries at the selected delivery point. Such adhesive delivery can be used to secure a medical device to the patient or to repair a diseased or damaged tissue by providing support through the adhesive. For example, a weakened tissue structure can be reinforces with the adhesive.

Specific Embodiments of Interest

Embolic Protection Devices

Embolic protection devices are used to prevent the incidence of ischemic adverse events associated with embolus in vascular vessels occluding oxygenated blood to distal organs or tissues. Embolic protection devices (EPD) are described in copending U.S. patent application Ser. No. 10/414,909 now U.S. Pat. No. 7,303,575 to Ogle, entitled "Embolism Protection Devices," incorporated herein by reference and copending provisional U.S. Patent Application Ser. No. 60/489,044, filed Jul. 22, 2003 to Ogle et al., entitled "Embolism Protection Device," incorporated herein by reference. In relation to present embodiments, the embolism protection device comprises biocompatible polymer SCF fibers. With appropriate designs, Embolic Protection Devices (EPD) incorporating SCF fibers can have two desirable properties. First, the devices with the fibers are able to conform to the complex and often asymmetrical contours of the vessel wall, thus avoiding open sites for escape of small-diameter emboli. Second, these devices can be particularly effective as a means of emboli disposal. Upon device removal, emboli are likely lodged in the device, to reduce the chance of the emboli reentering the circulation.

The device can consists of a polymeric fiber matrix to be delivered distal to the site of surgical intervention and subsequently expanded to fill the vessel(s) of interest. (See, for example, schematic depiction in FIG. 2.) Entry and deployment of the device are accomplished with limited vessel trauma, and once in place the matrix can capture emboli, in some embodiments, as small as 40 µm in diameter and, in some embodiments release a clot-busting agent which resolves entrapped emboli. The appropriate number of fibers for the bundle can be selected empirically to yield the desired packing density in the resulting mat and corresponding effective pore size. All this is accomplished while maintaining flow of blood elements through the vessel. In one embodiment, the fibers are attached to a guide wire to deliver to the vessel distal to the site of intervention where it is deployed. The polymer can expand upon release within a patient's vessel into a structure configured to filter flow through the vessel.

Referring to a schematic cross sectional view in FIG. 2, a device 100 is shown within a patient's vessel 102. Device 100 comprises a sheath 104, and an embolism protection structure 106. Structure 106 comprises a guide wire 120, an SCF fiber bundle 122 arranged along guide wire 120, and a microcatheter 124 that is placed over guide wire 120. Sheath 104 is a catheter like structure placed over structure 106. Fiber bundle 122 is secured to guide wire 120 at fastening point 126. This fastening to the guide wire can be accomplished with an adhesive, a mechanical fastening with a band or the like and/or other appropriate fastening approaches or combination of approaches. On their other end, fiber bundle 122 is attached over a small tube 128 that glides over guide wire 120. Upon deployment of structure 106 at a selected location, sheath 104 can be drawn back, as shown in FIG. 2B to expose fiber bundle 122 within vessel 102. By pushing against tube 128 with microcatheter 124, the ends of the fibers are drawn together to flair out the middle of the fibers to fill the vessel lumen, as shown in FIG. 2C. For removal from the patient, fiber bundle 122 can be drawn within a retraction device 130, as shown in FIG. 2D.

In addition, corresponding methods can be effective for reducing or eliminating adverse effects of an embolus. In some embodiments, the method comprises delivering an embolism protection device and administering a biologically active agent. The delivering of the embolism protection device can be performed within a vessel of a patient with the device being tethered with a tether such that the embolism protection device filters flow within the vessel.

Glue Compatible Substrates

A variety of approaches, such as suturing, stapling, clamping, adhering with adhesive and combinations thereof, can be used to secure implantation of a prosthesis. Selection of a particular approach can depend on the particular implantation procedure. An example is shown in FIG. 3. In this embodiment, a vascular graft 150 has a tubular portion 152 and two attachment portions 154, 156, respectively at each end of tubular portion 152. Attachment portions 154, 156 generally have SCF fibers along their surface. Attachment portions can be, for example, mats of woven or entangled SCF fibers or any other appropriate SCF fiber structure. The SCF fibers can be, for example, glued or chemically bonded to the tubular portion 152. Tubular portion 152 can be formed from biocompatible fabric, tissue, combinations thereof or other structures known in the art. For implantation of graft 150, the SCF fibers of the attachment portions are associated with a medical adhesive along their surface. The medical adhesive can then be adhered to a portion of native blood vessel to secure the graft to the vessel. The use of the SCF fibers in forming the adhesive bond can result in a stronger adhesive bond. With respect to these embodiments, the SCF fibers can be associated with a portion of the device being used to secure the device. Thus, the particular attachment section of the prosthesis can comprise SCF fibers to facilitate implantation using a medical adhesive. Thus, SCF fibers can be advantageously incorporated within prostheses to facilitate adherence of the device, although the fibers can be advantageously used for various other purposes and structures with a prosthesis. A prosthesis or portion thereof formed with SCF fibers associated with an adhesive can be formed as a substrate with a plurality of SCF fibers that are woven, entangled or chemically bonded to form the structure.

Repair Patches

SCF fibers can be advantageously used in the attachment of repair patches within a patient. For example, the repair patches can be a mat of SCF fibers or the SCF fibers can be attached at the surface of a patch material, such as a polyester or tissue patch. The SCF fibers can be secured to patch material, for example, with an adhesive or with chemical bonding. As an example, a surgical polyester patch is shown in FIG. 4A to repair a lung. The patch generally has good biocompatibility and good adhesion but the strength may not be the same that is necessary in patching the aorta, see FIG. 4B. Referring to FIG. 4A, lung 170 is shown with a surgical patch 172. Referring to FIG. 4B, arota 180 adjacent heart 182 is shown with an aorta patch 184. An expanded view of FIG. 4C depicts a cartoon showing a patient's tissue 190 bonded with an adhesive 192 to an SCF fiber 194. The repair patches can be considered a particular type of prosthesis.

In particular, the SCF fiber grooves can create a capillary system to adsorb the adhesives with an increased surface area, which increases the volume of adhesive for a given volume of fiber. Also, the surface grooves of the fiber provides for mechanical interlocking. Both these factors can increase the adhesive strength and permanence of the bond. The SCF fibers can be used to form an entire anchoring section of a prosthesis, or the fibers can be combined with other structures. For example, the fibers can be attached to a solid surface, such as a polymer surface, through adhesive attachment or chemical attachment, such as covalent crosslinking of the fibers with a polymer substrate.

Tendon Repair

Tendon rupture is becoming a significant disease treated by orthopedic surgeons. These repairs can be complicated by the fact that tendon reconstruction requires significant strength to bear the mechanical forces imparted by the active muscle. Medical devices incorporating SCF fibers can be used to the repair of injured/torn tendons. Referring to FIG. 5, a tendon 200 attached with muscle 202 is shown with a tendon patch 204. The attachment of the repair material to bridge the tear must be very strong. The SCF material offers advantages that you can use an adhesive instead of suture. Then, by distributing the load over the greater surface area of the adhesive bond, the repair would be more effective. In some embodiments, the repair matrix can be made of a high tensile strength polyester and optionally treated with growth factors to encourage cellular growth to form a seamless meshing between the tendon and repair matrix.

Drug Delivery Element

Delivery of bioactive agents to local areas from medical articles has been proposed as alternatives to systemic administration. These approaches are very attractive due to the reduced risk of systemic toxicity, increased effectiveness, and the potential for more controlled release with respect to time of administration and dose. An embodiment envisioned by this invention is the use of the SCF technology to deliver a drug to stimulate a bioactive response. For example, a number of small fiber particles could have anti-microbial agents associated to provide an antiseptic field for inter-operative suppression of infection. The SCF fiber particles can be formed from a grouping of entwined SCF fibers that may or may not be chemically crosslinked to each other. Referring to FIG. 6, a collection of SCF particles 210 is shown schematically. In the expanded view in the balloon of FIG. 6, a cartoon is shown with an SCF fiber 212 with an antimicrobial agent 214. The increased shape factor/surface area of the SCF structure can provide, for example, a factor of 3 times increased volume of the drug for a given volume of drug delivery material. The use of SCF particles formed from a sorbant polymer could result in a structure that did not need to be ultimately removed. In some embodiments, the element can be impregnated with gentamicine.

Vascular Closure Device

The number of less invasive endovascular procedures is on the rises. During the process of performing an endovascualar procedure, a puncture wound can be made in the patient's groin to provide access to the femeroal artery for access to the perform the vascular procedure. In principle, similar puncture wounds can be placed at other patient locations to access other blood vessels. Upon completion of the procedure, the wound requires significant pressure and time to close the incision. A vascular closure device can provide a matrix of SCF fibers to be placed into the wound, tamped down like embolic protection device. The SCF fibers optionally can be coated with pro-thormoblytic agents which would stop the blood flow. The device can be made of PLA or other resorbable polymer to be resorbed after the procedure. Referring to FIG. 7A, a patient's femor 220 is shown with a puncture 222 shown to access the femoral artery 224. In an expanded view in FIG. 7B, the puncture 222 is sealed with a vascular closure device 226 comprising SCF fibers. Vascular closure devices generally are described further in U.S. Pat. No. 5,690,674 to Diaz, entitled "Wound Closure With Plug," incorporated herein by reference.

Catheter with SCF Surface

Figure 8A:
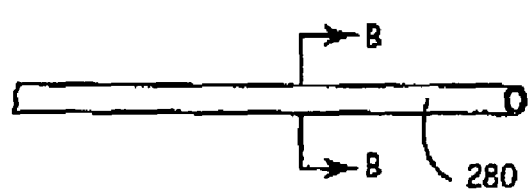
FIG. 8A is a perspective view of a catheter with a coating comprising SCF fibers.
Figure 8B:
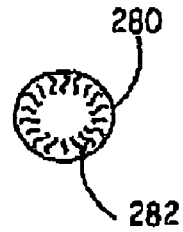
FIG. 8B is a schematic cross sectional view of the catheter of FIG. 8A showing the fibers along the inner catheter surface.

With the increase in performing more complex and anatomically smaller procedures, the advent of small biological catheters is required. Yet, catheters of very small size suffer from issues of thrombosis and occlusion. The embodiment envisioned her would provide for a small catheter with an internal SCF associated surface. The presence of the surface capillaries can facilitate flow to reduce thrombosis. In additional or alternatively, the SCF fibers can be associated with anti-coagulation agents and/or thrombolic agents. For example, the addition of heparin sulfate surface treatment to help provide for sustained flow of blood through a small catheter. The SCF fibers can be associated with the inner surface and/or the outer surface of the catheter, for example, with an adhesive or with chemical bonding, such as crosslinking. Referring to FIG. 8A, a micro-catheter 280 is shown schematically. Referring to FIG. 8B, a further expanded view cross sectional view of microcatheter 280 is shown with SCF fibers 282 along the inner surface. The size of the catheter can be selected by a person of ordinary skill in the art based on the selected use.

Aneurysm Repair Matrix

Vascular aneurysm is a significant problem affecting many people per year. If not treated the rupture can be fatal. An example of an embodiment of an aneurysm repair matrix is comprised of one or more SCF fibers. For example, a small SCF fiber can be placed in the aneurysm via a small catheter. The fiber cam be coated with a pro-thrombotic drug to provide a dose of clotting agent, the shape factor would almost triple the amount of drug that could be coated. Since the fibers are soft and deformable, to completely envelope the aneurysm, the fiber is easy to packed. If the pro-thromotic agent is released slowly, the blood can envelope the fiber because the flow character of the capillary network. The aneurysm can be completely enveloped and repaired.

Figure 9A:
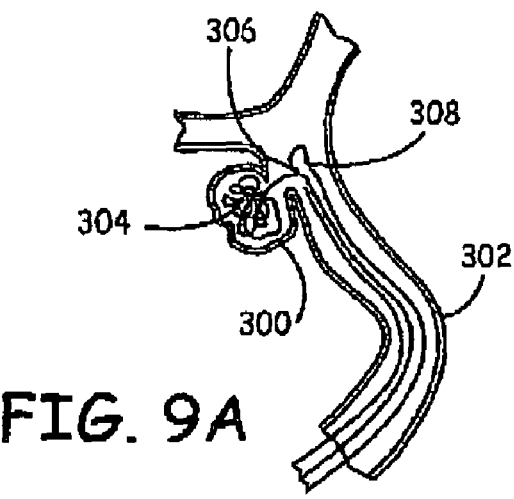
FIG. 9A is a schematic view showing an SCF fiber being associated with an aneurysm.
Figure 9B:
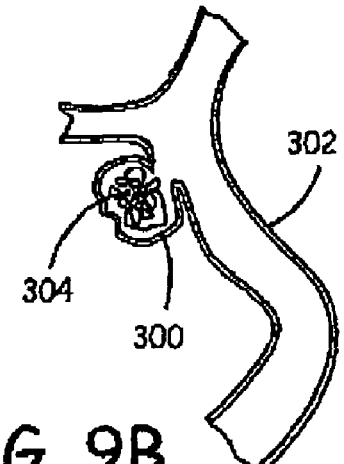
FIG. 9B is a schematic view of the aneurysm of FIG. 9A enveloped with the SCF fiber.

This embodiment is shown schematically in FIG. 9. In FIG. 9A, an aneurysm 300 is depicted in the middle cerebral artery 302. An SCF fiber 304 is delivered through a side port 306 in a catheter 308. As shown in FIG. 9B, the catheter has been removed, and aneurysm 300 is enveloped with SCF fiber 304.

Artificial Liver

Some artificial livers use a chamber system comprising two chambers filled with cartridges that contain liver cells. This is similar to a dialysis machine, such that when the device is connected to blood vessels, the blood is filtered, and returned circulatory system.

Figure 10:
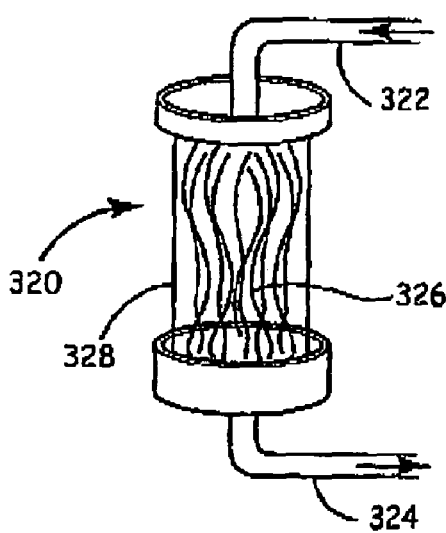
FIG. 10 is a side view of an artificial liver.
Figure 11:
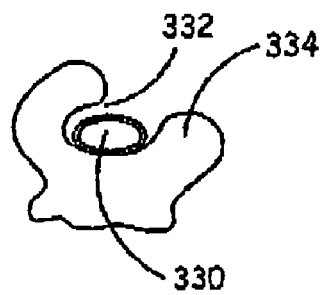
FIG. 11 is a schematic, fragmentary cross sectional view of an SCF fiber associated with a liver cell.
Figure 12:
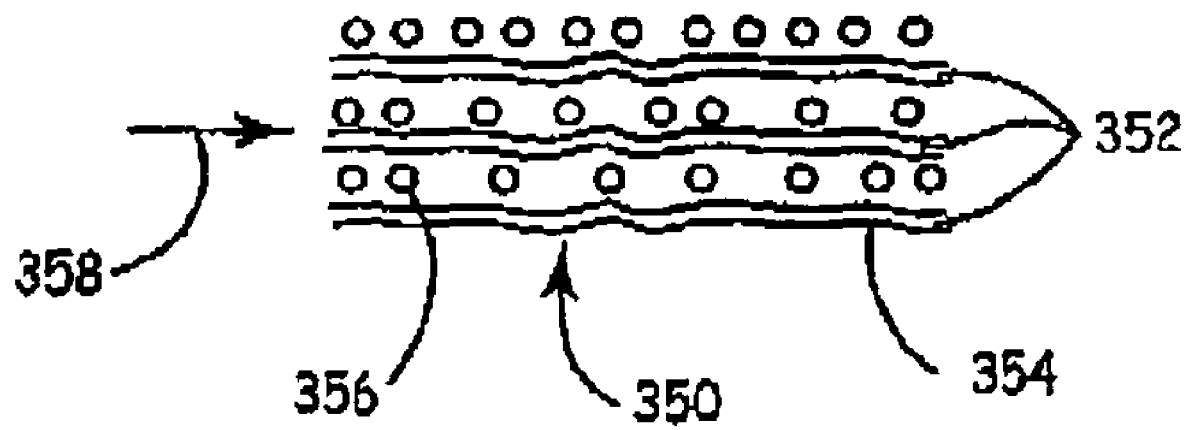
FIG. 12 is a side view of a synthetic heart muscle comprising layers of SCF fiber mats and heart muscle cells.

The use of SCF fibers would be very useful in this embodiment for the following reasons: the fibers have a ~2.8 shape factor which increases the surface area available for cell colonization; the grooves create natural topography (low areas) to facilitate colonized cells; the fiber manages fluid flow very well thus creating a great matrix to flow blood across the fiber; and the SCF has groves which can be packed very closely due to their special shape. Referring to FIG. 10, an artificial liver 320 is shown with an inflow 322, an outflow 324 and a matrix of SCF fibers and liver cells 326 within a cavity 328 between inflow 322 and outflow 324. Referring to FIG. 11, a liver cell 330 is shown schematically in a surface channel 332 of an SCF fiber 334.

Bio Artificial Heart Muscle

Heart cells have been shown to be able to grow in vitro in monolayer sheets. These sheets when exposed to an electrical pulse can elicit contractile force by the artificial muscle. This technique is limited when the number of cell layers increase because there is no means to provide microvascularture to feed the cells. This embodiment envisions the SCF fiber creating that microvascular structure to first grow the tissue equivalent, and then provide micro vascularture when implanted. Referring to FIG. 11, a synthetic heart muscle tissue 350 is depicted with a plurality of layers 352 comprising SCF fiber bundles 354 and heart cells 356. Blood flow is shown schematically with a flow arrow 358.

Regenerated Nerve Endings

Figure 13:
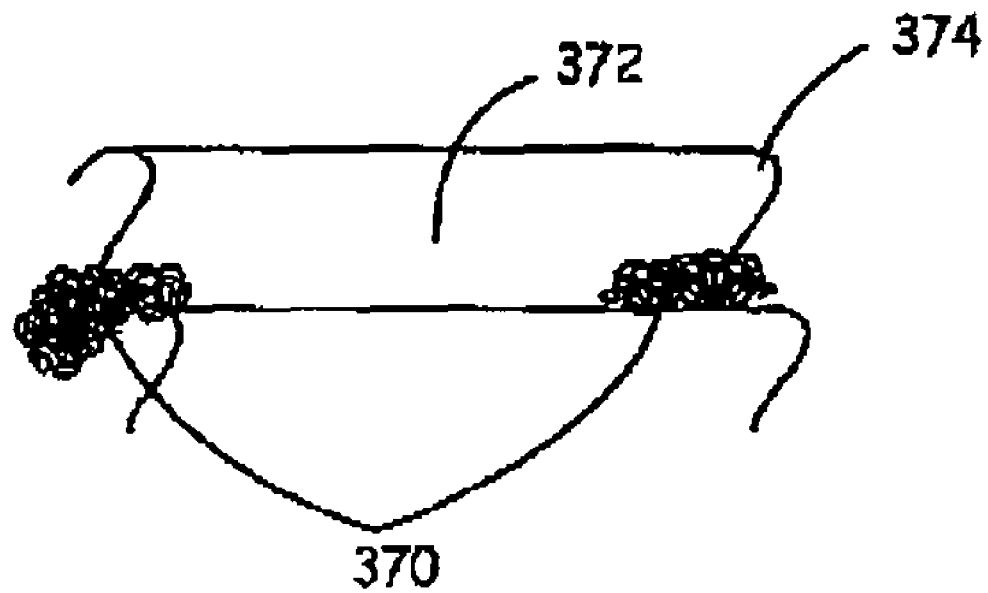
FIG. 13 is a schematic view of nerve cells within a surface capillary of a fiber.

Correction of problems associated with nerve damage can involve regeneration of a nerve connection. This regeneration of a connection has been shown to be helped by providing a path of growth factors and channels to reconnect the nerve ending. In some embodiments, the SCF matrix channels nerve growth factor (NGF) to the side to stimulate the reconnection of nerve endings. As depicted schematically in FIG. 13, nerve cells 370 are shown colonizing capillary 372 in an SCF fiber 374.

Completion of the Medical Device, Storage, Packaging, Distribution and Use

The SCF substrate can form an entire medical device itself, or the fiber can be incorporated with other biocompatible components into a medical device. For example, a SCF composite forming a tendon repair kit can be incorporated into a tissue tendon prosthesis, prior to storage and/or distribution of the resulting prosthesis. Depending on the particular device, the final assembly of the device can be completed by the user. If the fibers are associated with a bioactive agent, the device may or may not be stored with the bioactive agent associated with the device, as appropriate. The presence of a bioactive agent may involve particular storage considerations, such as refrigeration, which can be selected appropriately.

The SCF material can be stored appropriately prior to or following formation into a medical device. Generally, the fibers or a composite with the fibers is stored in a dry, sterile environment. If components of the medical device require moisture to maintain their integrity, such as tissue components with or without viable cells, the medical device with the fiber composite can be stored in a moist, sterile environment. The moist environment can be maintained with or without immersing the medical device in a sterile liquid, such as aqueous glutaraldehyde.

For distribution, the medical device is placed in sealed and sterile containers. The containers can be dated such that the date reflects the maximum advisable storage time, if components of the medical device should not be stored indefinitely. The containers are packaged along with instructions for the proper use and/or implantation of the medical device and along with other appropriate and/or required labeling. The containers are distributed to health care professionals for use in appropriate medical procedures, such as implantation of a prosthesis and the like.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A method for delivering a bioactive agent using a medical device, the method comprising contacting a patient's body fluids/tissues with a plurality of surface capillary fibers associated with at least a portion of a surface of the device, wherein the surface capillary fibers are pre-loaded and in association with a bioactive agent that elutes in a controlled way from the fibers upon contacting the fluids/tissues, wherein each of the surface capillary fibers comprises at least one capillary along its outer surface running along at least a portion of the length of the surface capillary fiber, wherein the medical device is a percutaneous device having the plurality of surface capillary fibers associated with a portion of the device to be placed within the patient, or is an implantable device, and wherein the bioactive agent is associated with a controlled release agent.

2. The method of claim 1 wherein the medical device is a prosthetic device.

3. The method of claim 1 wherein the medical device is a catheter.

4. The method of claim 3 wherein the catheter comprises a lumen and the surface capillary fibers are associated with the lumen of the catheter.

5. The method of claim 1 wherein the bioactive agent is selected from the group consisting of a thrombolytic agent, an anti-platelet agent, an anti-coagulation agent, a growth factor or a combination thereof.

6. The method of claim 1 wherein the plurality of surface capillary fibers are associated with at least a portion of a surface of the device with an adhesive, mechanical binding, heat bonding, or chemical bonding.

7. The method of claim 1 wherein the bioactive agent is selected from a group consisting of an anti-microbial agent, a thrombolytic agent, an anti-platelet agent, an anti-coagulation agent, a growth factor or a combination thereof.

8. The method of claim 1 wherein the bioactive agent comprises a thrombolytic agent.

9. The method of claim 1 wherein the bioactive agent comprises tissue plasminogen activator.

10. The method of claim 1 wherein the bioactive agent comprises an anti-microbial agent.

11. The method of claim 1 wherein the device is configured for placement within a blood vessel without blocking flow through the vessel.

12. A medical device comprising:
a plurality of surface capillary fibers associated with at least a portion of a surface of the device, the surface capillary fibers comprising a polymer, and
a quantity of bioactive agent pre-loaded and in association with the surface capillary fibers,
wherein the bioactive agent elutes in a controlled way from the fibers when the surface capillary fibers are in contact with a patient's body fluids/tissue,
wherein each of the surface capillary fibers comprises at least one capillary along its outer surface running along at least a portion of the length of the surface capillary fiber,
wherein the medical device is a percutaneous device or is an implantable device, and
wherein the bioactive agent is associated with a controlled release agent.

13. The medical device of claim 12 wherein the plurality of surface capillary fibers are associated with at least a portion of a surface of the device with an adhesive, mechanical binding, heat bonding, or chemical bonding.

14. The medical device of claim 12 wherein the bioactive agent is selected from a group consisting of an anti-microbial agent, a thrombolytic agent, an anti-platelet agent, an anti-coagulation agent, a growth factor or a combination thereof.

15. The medical device of claim 12 wherein the bioactive agent comprises a thrombolytic agent.

16. The medical device of claim 12 wherein the bioactive agent comprises tissue plasminogen activator.

17. The medical device of claim 12 wherein the bioactive agent comprises an anti-microbial agent.

18. The medical device of claim 12 wherein each of the surface capillary fibers has a surface area of at least about a factor of 1.5 greater than a corresponding circular fiber with an equivalent diameter.

19. The medical device of claim 12 wherein the device is configured for placement within a blood vessel without blocking flow through the vessel.

20. The medical device of claim 12 wherein the device comprises a catheter and additional surface capillary fibers, wherein the additional surface capillary fibers are associated with the inner surface of the catheter.

21. A medical device, comprising:
a plurality of surface capillary fibers associated with at least a portion of a surface of the device, the surface capillary fibers comprising a polymer matrix, and
a quantity of bioactive agent pre-loaded within the polymer matrix of the surface capillary fibers,
wherein the bioactive agent elutes in a controlled way from the fibers when the surface capillary fibers are in contact with a patient's body fluids/tissue,
wherein each of the surface capillary fibers comprises at least one capillary along its outer surface running along at least a portion of the length of the surface capillary fiber, and wherein the medical device is a percutaneous device or an implantable device.

22. The medical device of claim 21 wherein the bioactive agent is selected from a group consisting of an anti-microbial agent, a thrombolytic agent, an anti-platelet agent, an anti-coagulation agent, a growth factor or a combination thereof.

23. The medical device of claim 21 wherein the bioactive agent comprises a thrombolytic agent.

24. The medical device of claim 21 wherein the bioactive agent comprises tissue plasminogen activator.

25. The medical device of claim 21 wherein the bioactive agent comprises an anti-microbial agent.

* * * * *